US012656253B2

(12) United States Patent
Hou et al.

(10) Patent No.: US 12,656,253 B2
(45) Date of Patent: Jun. 16, 2026

(54) METHOD FOR PREDICTING AMOUNT OF RECOVERABLE OIL AND GAS RESOURCES FROM IN-SITU CONVERSION OF SHALE

(71) Applicant: PetroChina Company Limited, Beijing (CN)

(72) Inventors: Lianhua Hou, Beijing City (CN); Jinhua Fu, Beijing City (CN); Tao Jiang, Beijing City (CN); Yuhua Wang, Beijing City (CN); Xianyang Liu, Beijing City (CN); Jinghong Wang, Beijing City (CN); Yongxin Li, Beijing City (CN)

(73) Assignee: PetroChina Company Limited, Beijing (CN)

( * ) Notice: Subject to any disclaimer, the term of this patent is extended or adjusted under 35 U.S.C. 154(b) by 563 days.

(21) Appl. No.: 18/154,555

(22) Filed: Jan. 13, 2023

(65) Prior Publication Data

US 2023/0175961 A1 Jun. 8, 2023

Related U.S. Application Data

(63) Continuation of application No. PCT/CN2021/104637, filed on Jul. 6, 2021.

(30) Foreign Application Priority Data

Jul. 15, 2020 (CN) .......................... 202010678399.4

(51) Int. Cl.
$G01N\ 21/55$ (2014.01)
$G01N\ 33/24$ (2006.01)

(52) U.S. Cl.
CPC ............. *G01N 21/55* (2013.01); *G01N 33/24* (2013.01)

(58) Field of Classification Search
CPC ............................... G01N 21/55; G01N 33/24
See application file for complete search history.

(56) References Cited

U.S. PATENT DOCUMENTS 8,738,295 B2 5/2014 Baez et al.
2015/0120169 A1 4/2015 Horst et al.
(Continued)

FOREIGN PATENT DOCUMENTS

CN 102707333 A 10/2012
CN 104297448 A 1/2015
(Continued)

OTHER PUBLICATIONS

Zhang B., et al., "Kinetic Simulation Of Hydrocarbon Generation And Its Application To In-Situ Conversion Of Shale Dil," Petroleum Exploration and Development, 46(6): 1212-1219 (2019).
GB/T 19145, ICS 75.010, E 11 "Determination of Total Organic Carbon in Sedimentary Rock" (2003).
SY/T 5124, ICS 75-010 "Method of Determining Microscopically the Reflectance of Vitrinite in Sedimentary" (2012).
(Continued)

*Primary Examiner* — Michael J Dalbo
*Assistant Examiner* — Kaleria Knox
(74) *Attorney, Agent, or Firm* — Hamilton, Brook, Smith & Reynolds, P.C.

(57) ABSTRACT

The present disclosure provides a method for predicting the amount of recoverable oil and gas resources from in-situ conversion of shale. The method can quantitatively evaluate the amount of the recoverable oil resource and the amount of the recoverable gas resource from in-situ conversion of shale with different TOC and Ro and improve the prediction accuracy and efficiency for the amount of the recoverable oil and gas resources from in-situ conversion of shale.

15 Claims, 12 Drawing Sheets

(56) References Cited

U.S. PATENT DOCUMENTS

| | | | | |
|---|---|---|---|---|
| 2015/0247940 A1* | 9/2015 | de Matos Ravanelli | .................. | G01V 1/30 |
| | | | | 703/10 |
| 2016/0139293 A1* | 5/2016 | Misra | ..................... | G01V 3/30 |
| | | | | 702/7 |
| 2020/0018740 A1 | 1/2020 | Hou et al. | | |

FOREIGN PATENT DOCUMENTS

| | | | | | |
|---|---|---|---|---|---|
| CN | 104697914 A | | 6/2015 | | |
| CN | 105158816 A | | 12/2015 | | |
| CN | 105697003 A | | 6/2016 | | |
| CN | 106483268 A | | 3/2017 | | |
| CN | 107545512 A | | 1/2018 | | |
| CN | 108088779 A | | 5/2018 | | |
| CN | 108222925 A | | 6/2018 | | |
| CN | 108547612 A | * | 9/2018 | ............. | E21B 41/00 |
| CN | 109113699 A | | 1/2019 | | |
| CN | 109113730 A | * | 1/2019 | ............. | E21B 49/00 |
| CN | 109633778 A | | 4/2019 | | |
| CN | 110318744 A | | 10/2019 | | |
| EP | 2979224 A1 | | 2/2016 | | |
| RU | 2604565 C2 | | 11/2016 | | |

OTHER PUBLICATIONS

Supplemental search report issued on Dec. 25, 2022 for counterpart Chinese patent application No. 202010678399.4, along with machine EN translation, entitled "Method For Predicting Amount Of Recoverable Oil And Gas Resources From In-Situ Conversion Of Shale.".

Chinese Search Report issued on Jun. 22, 2020 or counterpart Chinese patent application No. 202010678399.4, along with machine EN translation, entitled "Method For Predicting Amount Of Recoverable Oil And Gas Resources From In-Situ Conversion Of Shale.".

Chinese Search Report issued on Dec. 8, 2022 or counterpart Chinese patent application No. 202010678399.4, along with machine EN translation, entitled "Method For Predicting Amount Of Recoverable Oil And Gas Resources From In-Situ Conversion Of Shale.".

International Search Report on Patentability for Int'l Application No. PCT/CN2021/104637. Date of Issuance Jan. 17, 2023, entitled "Method For Predicting Amount Of Recoverable Oil And Gas Resources From In-Situ Conversion Of Shale.".

International Search Report and Written Opinion for Int'l Application No. PCT/CN2021/104637. Date of Issuance Aug. 30, 2021, entitled "Method For Predicting Amount Of Recoverable Oil And Gas Resources From In-Situ Conversion Of Shale.".

* cited by examiner acquiring a total organic carbon content and vitrinite reflectance of shale to be measured — 101 establishing a prediction model of the amount of recoverable oil from in-situ conversion of shale, and acquiring the amount of recoverable oil of the shale to be measured on the basis of the total organic carbon content and the vitrinite reflectance of the shale to be measured by using the prediction model of the amount of recoverable oil from in-situ conversion of shale — 102 establishing a prediction model of the amount of recoverable gas from in-situ conversion of shale, and acquiring the amount of recoverable gas of the shale to be measured on the basis of the total organic carbon content and the vitrinite reflectance of the shale to be measured by using the prediction model of the amount of recoverable gas from in-situ conversion of shale — 103 acquiring a lower limit value of the amount of recoverable oil per unit mass of rock from in-situ conversion of shale on the basis of a lower limit value of the amount of cumulative oil output by one producing well group from in-situ conversion of shale and the rock mass of an effective heating region controlled by the producing well group — 104 establishing a prediction model of a lower limit value of the total organic carbon content of the effective shale, and acquiring the lower limit value of the total organic carbon content of the effective shale on the basis of a lower limit value of the amount of recoverable oil per unit mass of rock from in-situ conversion of shale and the vitrinite reflectance of the shale to be measured — 105 acquiring the effective thickness of shale, an effective thickness interval and an effective shale distribution region from in-situ conversion of shale on the basis of the total organic carbon content of the region to be evaluated interpreted by logging and the lower limit value of the total organic carbon content of the effective shale — 106 respectively establishing a model of an abundance value of a recoverable oil resource and a model of an abundance value of a recoverable gas resource in the effective thickness interval, and respectively acquiring the abundance value of the recoverable oil resource and the abundance value of the recoverable gas resource in the effective thickness interval of an evaluated well on the basis of the amount of recoverable oil per unit mass of rock and the amount of recoverable gas per unit mass of rock of a logging interpretation point — 107 respectively establishing a prediction model of the amount of a recoverable oil resource and a prediction model of the amount of a recoverable gas resource, and acquiring the amount of the recoverable oil resource and the amount of the recoverable gas resource on the basis of the prediction models for the amount of a recoverable oil resource and the amount of a recoverable gas resource — 108

FIG. 1 simulation temperature of pyrolysis/ °C

METHOD FOR PREDICTING AMOUNT OF RECOVERABLE OIL AND GAS RESOURCES FROM IN-SITU CONVERSION OF SHALE

CROSS-REFERENCE TO RELATED APPLICATIONS

This application is a continuation of International Application No. PCT/CN2021/104637, filed on Jul. 6, 2021, which claims priority to Chinese Patent Application No. 202010678399.4, filed on Jul. 15, 2020, both of which are hereby incorporated by reference in their entireties.

TECHNICAL FIELD

The present disclosure relates to a method for predicting the amount of recoverable oil and gas resources from in-situ conversion of shale and belongs to the technical field of oil and gas exploration and development.

BACKGROUND

Shale refers to sedimentary rock with a high total organic carbon content (TOC) and laminated foliation. When the maturity of the shale is low, i.e., the vitrinite reflectance (Ro) is less than 1.0%, pores in the shale are not developed, fluid flow is difficult and commercial scale development cannot be achieved with the existing horizontal well volume fracturing technology, but the in-situ conversion technology can be used to develop the shale with low maturity. The in-situ conversion technology is a technology that converts unconverted organic matter in the shale into oil and gas with an in-situ heating method, and extracts the in-situ converted oil and gas and oil and gas trapped in the shale simultaneously. The shale herein is a collective term for shale with medium and low maturity, that is, the shale with Ro less than 1.0%, including the shale with medium and low maturity and immature oil shale.

According to estimation from preliminary research, the amount of worldwide recoverable resources from in-situ conversion of the shale is greater than 1.5 trillion tons and the amount of recoverable resources from the natural gas technology is about 1,300 trillion cubic meters; the amount of a recoverable resource from in-situ conversion of the shale in China is greater than 80 billion tons and the amount of a recoverable resource from natural gas is greater than 60 trillion cubic meters; it is more than three times of the amount of the recoverable resource from conventional oil and natural gas, which has huge potential.

There are two schemes in the prior art for predicting oil and gas output from in-situ conversion of shale oil with medium and low maturity, which can be used for reference to evaluate the amount of recoverable oil and gas resources, but there is still no prediction technology for the amount of a recoverable resource from in-situ conversion of shale. Firstly, on the basis of the original hydrogen to carbon ratio (H/C), original total organic carbon content (TOC) and Ro value of the shale, a model of the amount of generated oil and gas from the original state of the shale and a model of the amount of trapped oil and gas at different Ro stages are established; on the basis of the amount of the generated oil and gas and the amount of the trapped oil and gas, a model of the amount of output oil and gas is established; the amount of oil and gas resources output from in-situ conversion can be evaluated by extrapolation. Secondly, on the basis of the original hydrogen index (HI), original total organic carbon content (TOC) and Ro value of the shale, a model of the amount of generated oil and gas from the original state of the shale and a model of the amount of trapped oil and gas at different Ro stages are established; on the basis of the amount of the generated oil and gas and the amount of the trapped oil and gas, a model of the amount of output oil and gas is established; the amount of oil and gas resources output from in-situ conversion can be evaluated by extrapolation.

The two schemes for evaluating the amount of oil and gas output from the shale oil with medium and low maturity in the prior art both have drawbacks when predicting the amount of a recoverable resource from in-situ conversion by extrapolation: firstly, the original hydrogen to carbon ratio (H/C), original total organic carbon content (TOC) and Ro value of the shale must be obtained; while the shale itself has undergone thermal evolution to a certain degree and is not in its original state, it is difficult to accurately obtain the original H/C or original HI and original TOC of the shale by using the existing technology, so there is a large error in the amount of output oil and gas, which is obtained according to the original H/C or original HI and original TOC. Secondly, the amount of generated oil and gas from the original state of the shale and the amount of trapped oil and gas at different Ro stages must be determined so as to obtain the amount of output oil and gas based on the amount of the generated oil and gas and the amount of the trapped oil and gas; in the case where there is no shale in the original state and thermal simulation experiments are not carried out, the amount of the generated oil and gas and the amount of the trapped oil and gas cannot be accurately determined, so the amount of oil and gas output from in-situ conversion cannot be obtained, and the amount of recoverable oil and gas from the shale cannot be obtained by extrapolation, either.

In summary, it is unable to accurately obtain the original H/C, original HI, original TOC, amount of generated oil and gas, and amount of trapped oil and gas of the shale with shale of thermal evolution to a certain degree by using the existing relevant technology, and thus it is unable to accurately carry out the research on the amount of oil and gas output from in-situ conversion of shale. At the same time, the evaluation technology for recoverable oil and gas resources from in-situ conversion of shale differs significantly from the existing technology, and the prediction technology for recoverable oil and gas resources from in-situ conversion of shale has not been developed yet.

Therefore, providing a novel method for predicting the amount of recoverable oil and gas resources from in-situ conversion of shale has become a technical problem urgently to be solved in this field.

SUMMARY

In order to overcome the defects described above, one object of the present disclosure is to provide a method for predicting the amount of recoverable oil and gas resources from in-situ conversion of shale.

Another object of the present disclosure is to provide an apparatus for predicting the amount of recoverable oil and gas resources from in-situ conversion of shale.

Yet another object of the present disclosure is to provide a computer device.

Still another object of the present disclosure is to provide a computer-readable storage medium. The present disclosure can quantitatively predict the amount of recoverable oil and gas resources from in-situ conversion of shale and improve the prediction accuracy and efficiency for the amount of the recoverable oil and gas resources from in-situ conversion of shale.

In order to achieve the above purpose, in one aspect, the present disclosure provides a method for predicting the amount of recoverable oil and gas resources from in-situ conversion of shale, wherein the method for predicting the amount of recoverable oil and gas resources from in-situ conversion of shale including:

acquiring a total organic carbon content and vitrinite reflectance of shale to be measured in a region to be evaluated;

establishing a prediction model of the amount of recoverable oil from in-situ conversion of shale, and acquiring the amount of recoverable oil of the shale to be measured on the basis of the total organic carbon content and the vitrinite reflectance of the shale to be measured by using the prediction model of the amount of recoverable oil from in-situ conversion of shale;

establishing a prediction model of the amount of recoverable gas from in-situ conversion of shale, and acquiring the amount of recoverable gas of the shale to be measured on the basis of the total organic carbon content and the vitrinite reflectance of the shale to be measured by using the prediction model of the amount of recoverable gas from in-situ conversion of shale;

establishing a prediction model of a lower limit value of the total organic carbon content of the effective shale, and acquiring the lower limit value of the total organic carbon content of the effective shale on the basis of a lower limit value of the amount of recoverable oil per unit mass of rock from in-situ conversion of shale and the vitrinite reflectance of the shale to be measured;

determining the effective thickness of shale, an effective thickness interval and an effective shale distribution region from in-situ conversion of shale on the basis of the total organic carbon content of the region to be evaluated interpreted by logging and the lower limit value of the total organic carbon content of the effective shale;

respectively establishing a model of an abundance value of a recoverable oil resource and a model of an abundance value of a recoverable gas resource in the effective thickness interval, and respectively acquiring the abundance value of the recoverable oil resource and the abundance value of the recoverable gas resource in the effective thickness interval of an evaluated well on the basis of the amount of recoverable oil per unit mass of rock and the amount of recoverable gas per unit mass of rock of a logging interpretation point; and respectively establishing a prediction model of the amount of a recoverable oil resource and a prediction model of the amount of a recoverable gas resource, and acquiring the amount of the recoverable oil resource and the amount of the recoverable gas resource on the basis of the prediction model of the amount of a recoverable oil resource and the prediction model of the amount of a recoverable gas resource.

In the method described above, preferably, establishing a prediction model of the amount of recoverable oil from in-situ conversion of shale, includes:

establishing a relationship model between the amount of output oil and the total organic carbon content on the basis of data of the amount of output oil acquired by performing thermal simulation experiments on a plurality of different shale samples, and the total organic carbon content and the vitrinite reflectance of the shale samples, and then extracting empirical parameters in the model to establish a model with the vitrinite reflectance, so as to establish the prediction model of the amount of recoverable oil from in-situ conversion of shale.

In the method described above, preferably, the prediction model of the amount of recoverable oil from in-situ conversion of shale is established according to the following formula:

$$Q_{po} = a_1 \times \left( \left( e^{a_2 Ro + a_3} \right) TOC - e^{a_4 Ro + a_5} \right) + a_6;$$

wherein, $Q_{po}$ is the amount of recoverable oil of the shale to be measured, mg/g·rock; Ro is the vitrinite reflectance of the shale to be measured, %; TOC is the total organic carbon content of the shale to be measured, wt %; $a_1$, $a_2$, $a_3$, $a_4$, $a_5$ and $a_6$ are the empirical parameters. g·rock in the unit mg/g·rock of the amount $Q_{po}$ of recoverable oil of the shale to be measured refers to the mass per g of rock.

In addition, a person skilled in the art may obtain the specific numerical values of the above empirical parameters $a_1$, $a_2$, $a_3$, $a_4$, $a_5$ and $a_6$ according to the result of the thermal simulation experiment in the region to be evaluated.

In the method described above, preferably, establishing a prediction model of the amount of recoverable gas from in-situ conversion of shale, includes:

establishing a relationship model between the amount of output gas and the total organic carbon content on the basis of data of the amount of output gas acquired by performing thermal simulation experiments on a plurality of different shale samples, and the total organic carbon content and the vitrinite reflectance of the shale samples, and then extracting empirical parameters in the model to establish a model with the vitrinite reflectance, so as to establish the prediction model of the amount of recoverable gas from in-situ conversion of shale.

In the method described above, preferably, the prediction model of the amount of recoverable gas from in-situ conversion of shale is established according to the following formula:

$$Q_{pg} = b_1 \times \begin{cases} \left( b_2 e^{b_3 Ro} \right) TOC + b_4 \ln Ro + b_5 & Ro \le w_1 \\ \left( b_6 \ln Ro + b_7 \right) TOC + b_8 Ro^2 + b_9 Ro + b_{10} & w_1 < Ro \le w_2; \\ \left( b_{11} Ro^{b_{12}} \right) TOC + b_{13} Ro^2 + b_{14} Ro + b_{15} & Ro \ge w_2 \end{cases}$$

wherein, $Q_{pg}$ is the amount of recoverable gas of the shale to be measured, m³/t·rock; Ro is the vitrinite reflectance of the shale to be measured, %; TOC is the total organic carbon content of the shale to be measured, wt %; $b_1$, $b_2$, $b_3$, $b_4$, $b_5$, $b_6$, $b_7$, $b_8$, $b_9$, $b_{11}$, $b_{12}$, $b_{13}$, $b_{14}$ and $b_{15}$ are the empirical parameters; $w_1$ is 0.5%-1.0%, and $w_2$ is 1.0%-1.4%.

t·rock in the unit m³/t·rock of the amount $Q_{pg}$ of recoverable gas of the shale to be measured refers to the mass per ton of rock.

In addition, a person skilled in the art may obtain the specific numerical values of the above empirical parameters $b_1$, $b_2$, $b_3$, $b_4$, $b_5$, $b_6$, $b_7$, $b_8$, $b_9$, $b_{10}$, $b_{11}$, $b_{12}$, $b_{13}$, $b_{14}$ and $b_{15}$ according to the result of the thermal simulation experiment in the region to be evaluated.

In the method described above, preferably, the lower limit value of the amount of recoverable oil per unit mass of rock from in-situ conversion of shale is acquired on the basis of a lower limit value of the amount of cumulative oil output by any producing well group in the same development region (the same development region refers to a development region with similar geological conditions of in-situ conversion and similar development processes) from in-situ conversion of shale and the rock mass of an effective heating region controlled by the producing well group according to the following formula:

$$Q_{po\_limt} = \frac{Q_{oil\_limt}}{Wt_{rock}};$$

wherein, $Q_{po\_limt}$ is the lower limit value of the amount of recoverable oil per unit mass of rock from in-situ conversion of shale, mg/g·rock; $Q_{oil\_limt}$ is the lower limit value of the amount of cumulative oil output by one producing well group from in-situ conversion of shale, mg; $Wt_{rock}$ is the rock mass of the effective heating region controlled by the producing well group from in-situ conversion of shale, g.

In the method described above, preferably, establishing a prediction model of a lower limit value of the total organic carbon content of effective shale includes: on the basis of the prediction model of the amount of recoverable oil from in-situ conversion of shale and the lower limit value of the amount of recoverable oil per unit mass of rock from in-situ conversion of shale, establishing the prediction model of the lower limit value of the total organic carbon content of the effective shale according to the following formula:

$$TOC_{limt} = \frac{c_1 \times Q_{po\_limt} + e^{c_2 Ro+c_3} + c_4}{e^{c_5 Ro+c_6}};$$

wherein, $TOC_{limt}$ is the lower limit value of the total organic carbon content of the effective shale, wt %; $Q_{po\_limt}$ is the lower limit value of the amount of recoverable oil per unit mass of rock from in-situ conversion of shale, mg/g·rock; Ro is the vitrinite reflectance of the shale to be measured, %; $c_1, c_2, c_3, c_4, c_5$ and $c_6$ are empirical parameters.

A person skilled in the art may obtain the specific numerical values of the above empirical parameters $c_1, c_2, c_3, c_4, c_5$ and $c_6$ according to the result of the thermal simulation experiment in the region to be evaluated, the development process, the development cost, and the like.

In the method described above, preferably, the effective thickness of shale, the effective thickness interval and the effective shale distribution region from in-situ conversion of shale are determined on the basis of the total organic carbon content of the region to be evaluated interpreted by logging and the lower limit value of the total organic carbon content of the effective shale according to the following rules:

when the continuous thickness of shale with the total organic carbon content interpreted by logging greater than the lower limit value of the total organic carbon content of the effective shale is greater than a set value of 1-15 m, the set value of 5 m is used as the apparent effective thickness of shale, and a depth interval corresponding to the apparent effective thickness of shale is an apparent effective thickness interval; between two adjacent apparent effective thickness intervals, when the continuous thickness of shale with the total organic carbon content interpreted by logging less than the lower limit value of the total organic carbon content of the effective shale is less than a set value of 0.5-5 m, the set value is determined as 2 m, and this interval is calculated into the apparent effective thickness of shale; when the continuous thickness of shale with the total organic carbon content interpreted by logging less than the lower limit value of the total organic carbon content of the effective shale is greater than a set value of 0.5-5 m, the set value is determined as 2 m, and this interval is not calculated into the apparent effective thickness of shale;

when the apparent effective thickness of shale is greater than a set value of 3-15 m, the set value of 5 m is used as the apparent effective thickness of shale, the apparent effective thickness of shale is the effective thickness of shale, and an interval corresponding to the top and bottom of the effective thickness of shale is the effective thickness interval;

when the apparent effective thickness of shale is less than or equal to a set value of 3-15 m, the set value of 5 m is used as the apparent effective thickness of shale, however, the apparent effective thickness of shale cannot be used as the effective thickness of shale and thus cannot be used as an independently developed interval, and the amount of a recoverable resource is not calculated for this interval; when the longitudinal distance between two or more effective thickness intervals exceeds a preset thickness value of 0.5-5 m, each effective thickness interval will be treated separately as a separate effective thickness interval of shale, i.e., treated as an independent series of development strata;

obtaining the effective thickness distribution of shale in the evaluated region with a non-equidistant interpolation method on the basis of the effective thickness of shale at well points in an evaluated region, wherein the grid spacing of the non-equidistant interpolation method uses a preset value of 0.1-10 km (more preferably, 2 km), and when the effective thickness of shale in the evaluated region is greater than a preset value of 3-15 m of the effective thickness, 5 m is used as the boundary of the effective thickness distribution region of shale, and the region where the effective thickness of shale is greater than 5 m is the effective shale distribution region.

A person skilled in the art may calibrate logging information on the basis of the core analysis and assay result of a system coring well, and acquire logging interpretation data of the region to be evaluated;

the set value may be determined according to in-situ conversion needs and geological conditions;

the non-equidistant interpolation method includes a three-point method, a five-point method, a finite element method, a Kriging method, a linear interpolation method, a non-linear interpolation method and the like.

In the method described above, preferably, respectively establishing a model of an abundance value of a recoverable oil resource and a model of an abundance value of a recoverable gas resource in an effective shale interval, includes:

respectively establishing the model of the abundance value of the recoverable oil resource and the model of the abundance value of the recoverable gas resource in the effective shale interval according to the amount of recoverable oil and the amount of recoverable gas of rock in the effective thickness interval per unit area on the basis of the amount of recoverable oil and gas per unit mass of rock, logging spacing, rock density and the effective thickness interval.

In the method described above, preferably, the model of the abundance value of the recoverable oil resource and the model of the abundance value of the recoverable gas resource in the effective shale interval are respectively established according to the following formulas:

$$AOR = 10^{13} \times \sum_{i=1}^{n} (Q_{po\_i} \times L_{inter} \times \rho_i);$$

$$AGR = 10^{14} \times \sum_{i=1}^{n} (Q_{pg\_i} \times L_{inter} \times \rho_i);$$

wherein AOR is the abundance of the recoverable oil resource in the effective shale interval of the region to be evaluated, 10,000 tons/km$^2$; AGR is the abundance of the recoverable gas resource in the effective shale interval of the region to be evaluated, 100 million cubic meters/km$^2$; $Q_{po\_i}$ is the amount of recoverable oil per unit mass of rock of an ith logging point in the effective thickness interval of the region to be evaluated, mg/g·rock; $Q_{pg\_i}$ is the amount of recoverable gas per unit mass of rock of the ith logging point in the effective thickness interval of the region to be evaluated, m$^3$/t·rock; $\rho_i$ is the rock density value of the ith logging point in the effective thickness interval of the region to be evaluated, g/cm$^3$; $L_{inter}$ is the logging spacing of the evaluated well, m; n is the total number of logging points in the effective thickness interval, and n is an integer.

In the method described above, preferably, the amount of recoverable oil per unit mass of rock and the amount of recoverable gas per unit mass of rock of the logging interpretation point are acquired according to the following steps:

acquiring the total organic carbon content, the rock density value and the measured spacing value of the logging interpretation point in the effective shale interval on the basis of the total organic carbon content of the region to be evaluated interpreted by logging, and then, acquiring the amount of recoverable oil per unit mass of rock and the amount of recoverable gas per unit mass of rock of the logging interpretation point by the prediction model of the amount of recoverable oil from in situ conversion of shale and the prediction model of the amount of recoverable gas from in situ conversion of shale on the basis of the total organic carbon content, the rock density value and the measured spacing value of the logging interpretation point in the effective shale interval and the vitrinite reflectance of a well point in a target stratum.

In the method described above, abundance values of recoverable oil resources and abundance values of recoverable gas resources for all well points in the evaluated region can be acquired on the basis of the above-established model of the abundance value of the recoverable oil resource and the above-established model of the abundance value of the recoverable gas resource in the effective shale interval; then on the basis of the abundance values of the recoverable oil resources and the abundance values of the recoverable gas resources for all the well points in the evaluated region, planar distribution of the abundance of the recoverable oil resource and the abundance of the recoverable gas resource in the evaluated region can be obtained by using the non-equidistant interpolation methods such as the three-point method, the five-point method, the finite element method, the Kriging method, the linear interpolation method and the non-linear interpolation method; on the basis of the planar distribution, the abundance of a recoverable oil resource of a jth grid in the effective shale distribution region and the abundance of a recoverable gas resource of the jth grid in the effective shale distribution region can be obtained.

In a more preferred embodiment of the present disclosure, the non-equidistant interpolation grid spacing of the three-point method, the five-point method, the finite element method, the Kriging method, the linear interpolation method, the non-linear interpolation method and the like adopts a preset value of 0.1-10 km, preferably 2 km.

In the method described above, preferably, on the basis of the abundance of the recoverable oil and gas resources of grid points of the effective shale distribution region and the area of the effective shale distribution region, the prediction model of the amount of the recoverable oil resource and the prediction model of the amount of the recoverable gas resource are respectively established according to the following formulas:

$$NO = \sum_{j=1}^{m} (AOR_j \times A_j);$$

$$NG = \sum_{j=1}^{m} (AGR_j \times A_j);$$

wherein NO is the amount of the recoverable oil resource in the region to be evaluated, 10,000 tons; NG is the amount of the recoverable gas resource in the region to be evaluated, 100 million cubic meters; $AOR_j$ is the abundance of the recoverable oil resource of a jth grid in the effective shale distribution region, 10,000 tons/km$^2$; $AGR_j$ is the abundance of the recoverable gas resource of the jth grid in the effective shale distribution region, 100 million cubic meters/km$^2$; $A_j$ is the area of the jth grid in the effective shale distribution region, km$^2$; m is the number of grids in the effective shale distribution region, and m is an integer.

In another aspect, the present disclosure further provides an apparatus for predicting the amount of recoverable oil and gas resources from in-situ conversion of shale, wherein the apparatus for predicting the amount of recoverable oil and gas resources from in-situ conversion of shale comprising:

a data acquiring module, used for acquiring a total organic carbon content and vitrinite reflectance of shale to be measured in a region to be evaluated;

a module for establishing a prediction model of the amount of recoverable oil from in-situ conversion of shale, used for establishing the prediction model of the amount of recoverable oil from in-situ conversion of shale, and acquiring the amount of recoverable oil of the shale to be measured on the basis of the total organic carbon content and the vitrinite reflectance of the shale to be measured by using the prediction model of the amount of recoverable oil from in-situ conversion of shale;

a module for establishing a prediction model of the amount of recoverable gas from in-situ conversion of shale, used for establishing the prediction model of the amount of recoverable gas from in-situ conversion of shale, and acquiring the amount of recoverable gas of the shale to be measured on the basis of the total organic carbon content and the vitrinite reflectance of the shale to be measured by using the prediction model of the amount of recoverable gas from in-situ conversion of shale;

a module for establishing a prediction model of a lower limit value of the total organic carbon content of the effective shale, used for establishing the prediction model of the lower limit value of the total organic carbon content of the effective shale, and acquiring the lower limit value of the total organic carbon content of the effective shale on the basis of the lower limit value of the amount of recoverable oil per unit mass of rock from in-situ conversion of shale and the vitrinite reflectance of the shale to be measured;

a module for determining the effective thickness of shale, an effective thickness interval and an effective shale distribution region from in-situ conversion of shale, used for determining the effective thickness of shale, the effective thickness interval and the effective shale distribution region from in-situ conversion of shale on the basis of the total organic carbon content of the region to be evaluated interpreted by logging and the lower limit value of the total organic carbon content of the effective shale;

a module for establishing a model of an abundance value of a recoverable oil resource and a model of an abundance value of a recoverable gas resource in the effective thickness interval, used for respectively establishing the model of the abundance value of the recoverable oil resource and the model of the abundance value of the recoverable gas resource in the effective thickness interval, and respectively acquiring the abundance value of the recoverable oil resource and the abundance value of the recoverable gas resource in the effective thickness interval of an evaluated well on the basis of the amount of recoverable oil per unit mass of rock and the amount of recoverable gas per unit mass of rock of a logging interpretation point; and a module for establishing a prediction model of the amount of a recoverable oil resource and a prediction model of the amount of a recoverable gas resource, used for respectively establishing the prediction model of the amount of the recoverable oil resource and the prediction model of the amount of the recoverable gas resource, and acquiring the amount of the recoverable oil resource and the amount of the recoverable gas resource on the basis of the prediction model for the amount of the recoverable oil resource and the prediction model of the amount of the recoverable gas resource.

In the apparatus described above, preferably, the module for establishing a prediction model of the amount of recoverable oil from in-situ conversion of shale is specifically used for, establishing a relationship model between the amount of output oil and the total organic carbon content on the basis of data of the amount of output oil acquired by performing thermal simulation experiments on a plurality of different shale samples, and the total organic carbon content and the vitrinite reflectance of the shale samples, and then extracting empirical parameters in the model to establish a model with the vitrinite reflectance, so as to establish the prediction model of the amount of recoverable oil from in-situ conversion of shale.

In the apparatus described above, preferably, the module for establishing a prediction model of the amount of recoverable oil from in-situ conversion of shale is further used for establishing the prediction model of the amount of recoverable oil from in-situ conversion of shale according to the following formula:

$$Q_{po} = a_1 \times \left( \left( e^{a_2 Ro + a_3} \right) TOC - e^{a_4 Ro + a_5} \right) + a_6;$$

wherein, $Q_{po}$ is the amount of recoverable oil of the shale to be measured, mg/g·rock; Ro is the vitrinite reflectance of the shale to be measured, %; TOC is the total organic carbon content of the shale to be measured, wt %; $a_1$, $a_2$, $a_3$, $a_4$, $a_5$ and $a_6$ are the empirical parameters.

In the apparatus described above, preferably, the module for establishing a prediction model of the amount of recoverable gas from in-situ conversion of shale is specifically used for, establishing a relationship model between the amount of output gas and the total organic carbon content on the basis of data of the amount of output gas acquired by performing thermal simulation experiments on a plurality of different shale samples, and the total organic carbon content and the vitrinite reflectance of the shale samples, and then extracting empirical parameters in the model to establish a model with the vitrinite reflectance, so as to establish the prediction model of the amount of recoverable gas from in-situ conversion of shale.

In the apparatus described above, preferably, the module for establishing a prediction model of the amount of recoverable gas from in-situ conversion of shale is further used for establishing the prediction model of the amount of recoverable gas from in-situ conversion of shale according to the following formula:

$$Q_{pg} = b_1 \times \begin{cases} \left( b_2 e^{b_3 Ro} \right) TOC + b_4 \ln Ro + b_5 & Ro \le w_1 \\ \left( b_6 \ln Ro + b_7 \right) TOC + b_8 Ro^2 + b_9 Ro + b_{10} & w_1 < Ro \le w_2 \\ \left( b_{11} Ro^{b_{12}} \right) TOC + b_{13} Ro^2 + b_{14} Ro + b_{15} & Ro \ge w_2 \end{cases}$$

wherein, $Q_{pg}$ is the amount of recoverable gas of the shale to be measured, m³/t·rock; Ro is the vitrinite reflectance of the shale to be measured, %; TOC is the total organic carbon content of the shale to be measured, wt %; $b_1$, $b_2$, $b_3$, $b_4$, $b_5$, $b_6$, $b_7$, $b_8$, $b_9$, $b_{11}$, $b_{12}$, $b_{13}$, $b_{14}$ and $b_{15}$ are the empirical parameters; $w_1$ is 0.5%-1.0%, and $w_2$ is 1.0%-1.4%.

In the apparatus described above, preferably, the module for establishing a prediction model of a lower limit value of the total organic carbon content of effective shale includes a unit for acquiring a lower limit value of the amount of recoverable oil per unit mass of rock from in-situ conversion of shale, used for acquiring the lower limit value of the amount of recoverable oil per unit mass of rock from in-situ conversion of shale on the basis of a lower limit value of the amount of cumulative oil output by any producing well group in the same development region from in-situ conversion of shale and the rock mass of an effective heating region controlled by the producing well group according to the following formula:

$$Q_{po\_limt} = \frac{Q_{oil\_limt}}{Wt_{rock}};$$

wherein, $Q_{po\_limt}$ is the lower limit value of the amount of recoverable oil per unit mass of rock from in-situ conversion of shale, mg/g·rock; $Q_{oil\_limt}$ is the lower limit value of the amount of cumulative oil output by one producing well group from in-situ conversion of shale, mg; $Wt_{rock}$ is the rock mass of the effective heating region controlled by the producing well group from in-situ conversion of shale, g.

In the apparatus described above, preferably, the module for establishing a prediction model of a lower limit value of the total organic carbon content of effective shale is specifically used for establishing the prediction model of the lower limit value of the total organic carbon content of the effective shale on the basis of the prediction model of the amount of recoverable oil from in-situ conversion of shale and the lower limit value of the amount of recoverable oil per unit mass of rock from in-situ conversion of shale according to the following formula:

$$TOC_{limt} = \frac{c_1 \times Q_{po\_limt} + e^{c_2 Ro + c_3} + c_4}{e^{c_5 Ro + c_6}};$$

wherein $TOC_{limt}$ is the lower limit value of the total organic carbon content of the effective shale, wt %; $Q_{po\_limt}$ is the lower limit value of the amount of recoverable oil per unit mass of rock from in-situ conversion of shale, mg/g·rock; Ro is the vitrinite reflectance of the shale to be measured, %; $c_1, c_2, c_3, c_4,$ $c_5$ and $c_6$ are empirical parameters.

In the apparatus described above, preferably, the module for determining the effective thickness of shale, an effective thickness interval and an effective shale distribution region from in-situ conversion of shale is specifically used for determining the effective thickness of shale, the effective thickness interval and the effective shale distribution region from in-situ conversion of shale on the basis of the total organic carbon content of the region to be evaluated interpreted by logging and the lower limit value of the total organic carbon content of the effective shale according to the following rules:

when the continuous thickness of shale with the total organic carbon content interpreted by logging greater than the lower limit value of the total organic carbon content of the effective shale is greater than a set value of 1-15 m, the set value of 5 m is used as the apparent effective thickness of shale, and a depth interval corresponding to the apparent effective thickness of shale is an apparent effective thickness interval; between two adjacent apparent effective thickness intervals, when the continuous thickness of shale with the total organic carbon content interpreted by logging less than the lower limit value of the total organic carbon content of the effective shale is less than a set value of 0.5-5 m, the set value is determined as 2 m, and this interval is calculated into the apparent effective thickness of shale; when the continuous thickness of shale with the total organic carbon content interpreted by logging less than the lower limit value of the total organic carbon content of the effective shale is greater than a set value of 0.5-5 m, the set value is determined as 2 m, and this interval is not calculated into the apparent effective thickness of shale;

when the apparent effective thickness of shale is greater than a set value of 3-15 m, the set value of 5 m is used as the apparent effective thickness of shale, the apparent effective thickness of shale is the effective thickness of shale, and an interval corresponding to the top and bottom of the effective thickness of shale is the effective thickness interval;

when the apparent effective thickness of shale is less than or equal to a set value of 3-15 m, the set value of 5 m is used as the apparent effective thickness of shale, however, the apparent effective thickness of shale cannot be used as the effective thickness of shale and thus cannot be used as an independently developed interval, and the amount of a recoverable resource is not calculated for this interval; when the longitudinal distance between two or more effective thickness intervals exceeds a preset thickness value of 0.5-5 m, each effective thickness interval will be treated separately as a separate effective thickness interval of shale, i.e., treated as an independent series of development strata;

obtaining the effective thickness distribution of shale in the evaluated region with a non-equidistant interpolation method on the basis of the effective thickness of shale at well points in an evaluated region, wherein the grid spacing of the non-equidistant interpolation method uses a preset value of 0.1-10 km, and when the effective thickness of shale in the evaluated region is greater than a preset value of 3-15 m of the effective thickness, 5 m is used as the boundary of the effective thickness distribution region of shale, and the region where the effective thickness of shale is greater than 5 m is the effective shale distribution region.

In the apparatus described above, preferably, the module for establishing a model of an abundance value of a recoverable oil resource and a model of an abundance value of a recoverable gas resource in the effective thickness interval is specifically used for, respectively establishing the model of the abundance value of the recoverable oil resource and the model of the abundance value of the recoverable gas resource in the effective shale interval according to the amount of recoverable oil and the amount of recoverable gas of rock in the effective thickness interval per unit area on the basis of the amount of recoverable oil and gas per unit mass of rock, logging spacing, rock density and the effective thickness interval.

In the apparatus described above, preferably, the module for establishing a model of an abundance value of a recoverable oil resource and a model of an abundance value of a recoverable gas resource in the effective thickness interval is further used for respectively establishing the model of the abundance value of the recoverable oil resource and the model of the abundance value of the recoverable gas resource in the effective shale interval according to the following formulas:

$$AOR = 10^{13} \times \sum_{i=1}^{n} (Q_{po\_i} \times L_{inter} \times \rho_i);$$

$$AGR = 10^{14} \times \sum_{i=1}^{n} (Q_{pg\_i} \times L_{inter} \times \rho_i);$$

wherein AOR is the abundance of the recoverable oil resource in the effective shale interval of the region to be evaluated, 10,000 tons/km²; AGR is the abundance of the recoverable gas resource in the effective shale interval of the region to be evaluated, 100 million cubic meters/km²; $Q_{po\_i}$ is the amount of recoverable oil per unit mass of rock of an ith logging point in the effective thickness interval of the region to be evaluated, mg/g·rock; $Q_{pg\_i}$ is the amount of recoverable gas per unit mass of rock of the ith logging point in the effective thickness interval of the region to be evaluated, m³/t·rock; $\rho_i$ is the rock density value of the ith logging point in the effective thickness interval of the region to be evaluated, g/cm³; $L_{inter}$ is the logging spacing of the evaluated well, m; n is the total number of logging points in the effective thickness interval, and n is an integer.

In the apparatus described above, preferably, the module for establishing a model of an abundance value of a recoverable oil resource and a model of an abundance value of a recoverable gas resource in the effective thickness interval includes a unit for acquiring the amount of recoverable oil per unit mass of rock and the amount of recoverable gas per unit mass of rock of a logging interpretation point, used for:

acquiring the total organic carbon content, the rock density value and the measured spacing value of the logging interpretation point in the effective shale interval on the basis of the total organic carbon content of the region to be evaluated interpreted by logging, and then, acquiring the amount of recoverable oil per unit mass of rock and the amount of recoverable gas per unit mass of rock of the logging interpretation point by the prediction model of the amount of recoverable oil from in situ conversion of shale and the prediction model of the amount of recoverable gas from in situ conversion of shale on the basis of the total organic carbon content, the rock density value and the measured spacing value of the logging interpretation point in the effective shale interval and the vitrinite reflectance of a well point in a target stratum.

In the apparatus described above, preferably, the module for establishing a prediction model of the amount of a recoverable oil resource and a prediction model of the amount of a recoverable gas resource is specifically used for, on the basis of the abundance of the recoverable oil and gas resources of grid points of the effective shale distribution region and the area of the effective shale distribution region, respectively establishing the prediction model of the amount of the recoverable oil resource and the prediction model of the amount of the recoverable gas resource according to the following formulas:

$$NO = \sum_{j=1}^{m}(AOR_j \times A_j);$$

$$NG = \sum_{j=1}^{m}(AGR_j \times A_j);$$

wherein NO is the amount of the recoverable oil resource in the region to be evaluated, 10,000 tons; NG is the amount of the recoverable gas resource in the region to be evaluated, 100 million cubic meters; $AOR_j$ is the abundance of the recoverable oil resource of a jth grid in the effective shale distribution region, 10,000 tons/km²; $AGR_j$ is the abundance of the recoverable gas resource of the jth grid in the effective shale distribution region, 100 million cubic meters/km²; $A_j$ is the area of the jth grid in the effective shale distribution region, km²; m is the number of grids in the effective shale distribution region, and m is an integer.

In yet another aspect, the present disclosure further provides a computer device, including a memory, a processor and computer programs stored on the memory and capable of running on the processor, wherein the processor, when executing the computer programs, implements the steps of the above method for predicting the amount of recoverable oil and gas resources from in-situ conversion of shale.

In still another aspect, the present disclosure further provides a computer-readable storage medium, on which computer programs are stored, wherein the computer programs, when executed by a processor, implement the steps of the above method for predicting the amount of recoverable oil and gas resources from in-situ conversion of shale.

The technical solution of the present disclosure achieves the beneficial technical effects as follows.

Firstly, on the basis of the TOC value and the Ro value of the shale to be measured, and the pre-established prediction model of the amount of recoverable oil and prediction model of the amount of recoverable gas from in-situ conversation of shale, the amount of recoverable oil and the amount of recoverable gas of the shale to be measured are obtained, which overcomes the defect that in the prior art, only by acquiring the original HI or original H/C and original TOC of shale and the amount of oil and gas generated by immature shale and the amount of trapped oil and gas, can the amount of recoverable oil and the amount of recoverable gas be established, the defect that precision is low when recovering the original HI or original TOC by using shale that has experienced certain thermal evolution, and the defect that only by obtaining the amount of trapped oil and gas and the amount of generated oil and gas, can the amount of output oil and gas be acquired, and achieves the effect of using the current TOC and Ro of shale in the stratum to obtain the amount of recoverable oil and the amount of recoverable gas from in-situ conversion. Therefore, the present disclosure uses the prediction model of the amount of recoverable oil and the prediction model of the amount of recoverable gas from in-situ conversion of shale, which not only realizes the quantitative prediction of the amount of recoverable oil and gas from in-situ conversion of shale, but also improves the prediction accuracy for the amount of recoverable oil and gas from in-situ conversion of shale.

Secondly, the lower limit value of the amount of recoverable oil per unit mass of rock from in-situ conversion of shale is obtained on the basis of the lower limit value of the amount of cumulative oil output by any producing well group in the same development region (the same development region refers to a development region with similar geological conditions of in-situ conversion and similar development processes) from in-situ conversion of shale and the rock mass of an effective heating region controlled by one producing well group, and accordingly, the prediction model of the lower limit value of TOC of the effective shale is established, so as to obtain the lower limit value of TOC of the effective shale, so that the effective thickness of shale, the effective thickness interval and the effective shale distribution region are accurately obtained, which overcomes the defect that the lower limit value of TOC of the effective shale cannot be determined in the prior art, and the defect that the effective thickness of shale, the effective thickness interval and the effective shale distribution region cannot be accurately obtained.

Finally, on the basis of the TOC value of the region to be evaluated interpreted by logging, the rock density value, the measured spacing value, the Ro analysis and assay value (the vitrinite reflectance of the well point in the target stratum) and the effective thickness interval, and the pre-established prediction model of the amount of recoverable oil and prediction model of the amount of recoverable gas, the amount of recoverable oil per unit mass of rock and the amount of recoverable gas per unit mass of rock of the logging interpretation point are obtained; on the basis of the pre-established model of the abundance value of the recoverable oil resource and model of the abundance value of the recoverable gas source, the abundance value of the recoverable oil resource and the abundance value of the recoverable gas source are obtained; on the basis of the effective shale distribution region in the evaluated region, and the pre-established prediction model of the amount of the recoverable oil resource and prediction model of the amount of the recoverable gas resource, the amount of the recoverable oil resource and the amount of the recoverable gas resource are obtained, which overcomes the defect that parameter averages are used to calculate the relevant parameters in the prior art, and the defect of the actual situation that the non-linear relationship between the amount of the recoverable oil and gas resources and TOC cannot be reflected by using the parameter average, and achieves the calculation for different contributions of different TOC points in the longitudinal direction within the effective shale interval to the amount of the recoverable oil and gas resources.

In summary, the technical solution of the present disclosure can quantitatively predict the amount of the recoverable oil and gas resources from in-situ conversion of shale and improve the prediction accuracy and efficiency for the amount of the recoverable oil and gas resources from in-situ conversion of shale.

BRIEF DESCRIPTION OF THE DRAWINGS

FIG. 1 is a flow diagram of a method for predicting the amount of recoverable oil and gas resources from in-situ conversion of shale provided by an embodiment of the present disclosure;

DETAILED DESCRIPTION

Figure 2:
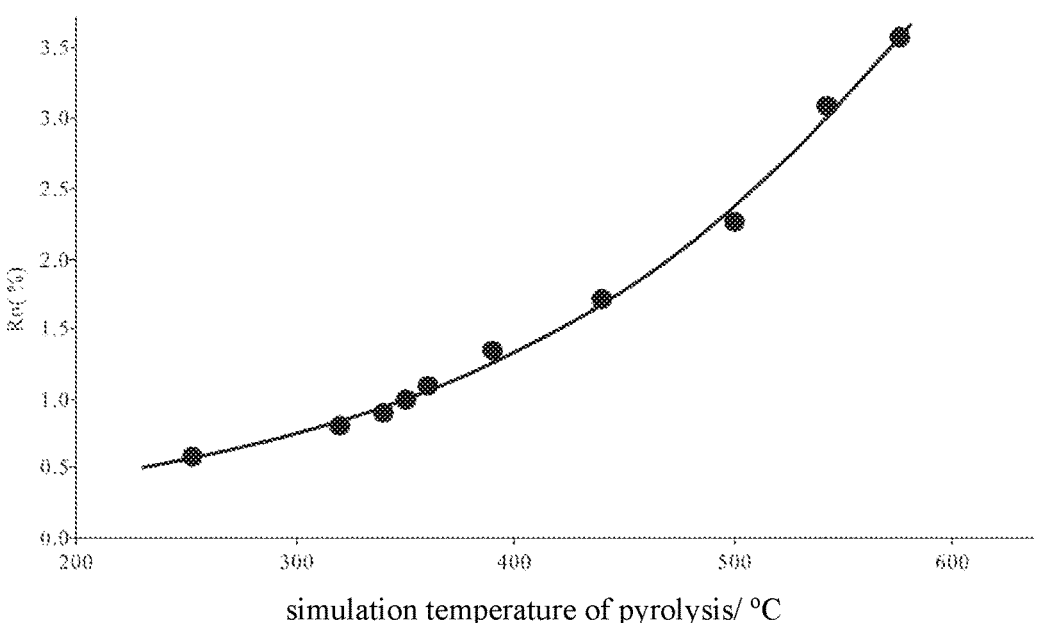
FIG. 2 is a relation diagram of a thermal simulation temperature and Ro in the embodiment of the present disclosure.

The technical solutions in embodiments of the present disclosure will be clearly and completely described below with reference to the accompanying drawings in the embodiments of the present disclosure. Apparently, the described embodiments are merely some rather than all of the embodiments of the present disclosure. All other embodiments obtained by a person of ordinary skill in the art based on the embodiments in the present disclosure without creative efforts shall fall within the protection scope of the present disclosure.

The in-situ conversion technology of shale for developing oil and gas is different from existing technologies and is disruptive. According to the in-situ conversion technology, light oil and natural gas are generated and output from unconverted organic matter and trapped oil in the stratum by artificial heating, and the in-situ conversion technology is applicable to immature shale-shale of medium and low maturity. The amount of recoverable oil and gas resources from in-situ conversion of shale is the key for development of in-situ conversion and controls the benefits of development of in-situ conversion. The technology for predicting the recoverable oil and gas resources from in-situ conversion is clearly different from the currently developed technology for evaluating oil and gas resources that have been generated and stored in the stratum. A completely new way of thinking and evaluation method is needed to predict the amount of recoverable oil and gas resources from in-situ conversion so as to meet the needs of site selection evaluation of in-situ conversion and exploration and development.

In order to overcome the defect that there are no technologies for predicting the amount of recoverable oil and gas resources from in-situ conversion of shale in the prior art, a solution for predicting the amount of recoverable oil and gas resources from in-situ conversion of shale is put forwards. The solution for predicting the amount of recoverable oil and gas resources from in-situ conversion of shale related in embodiments of the present disclosure is described in detail below.

Figure 1:
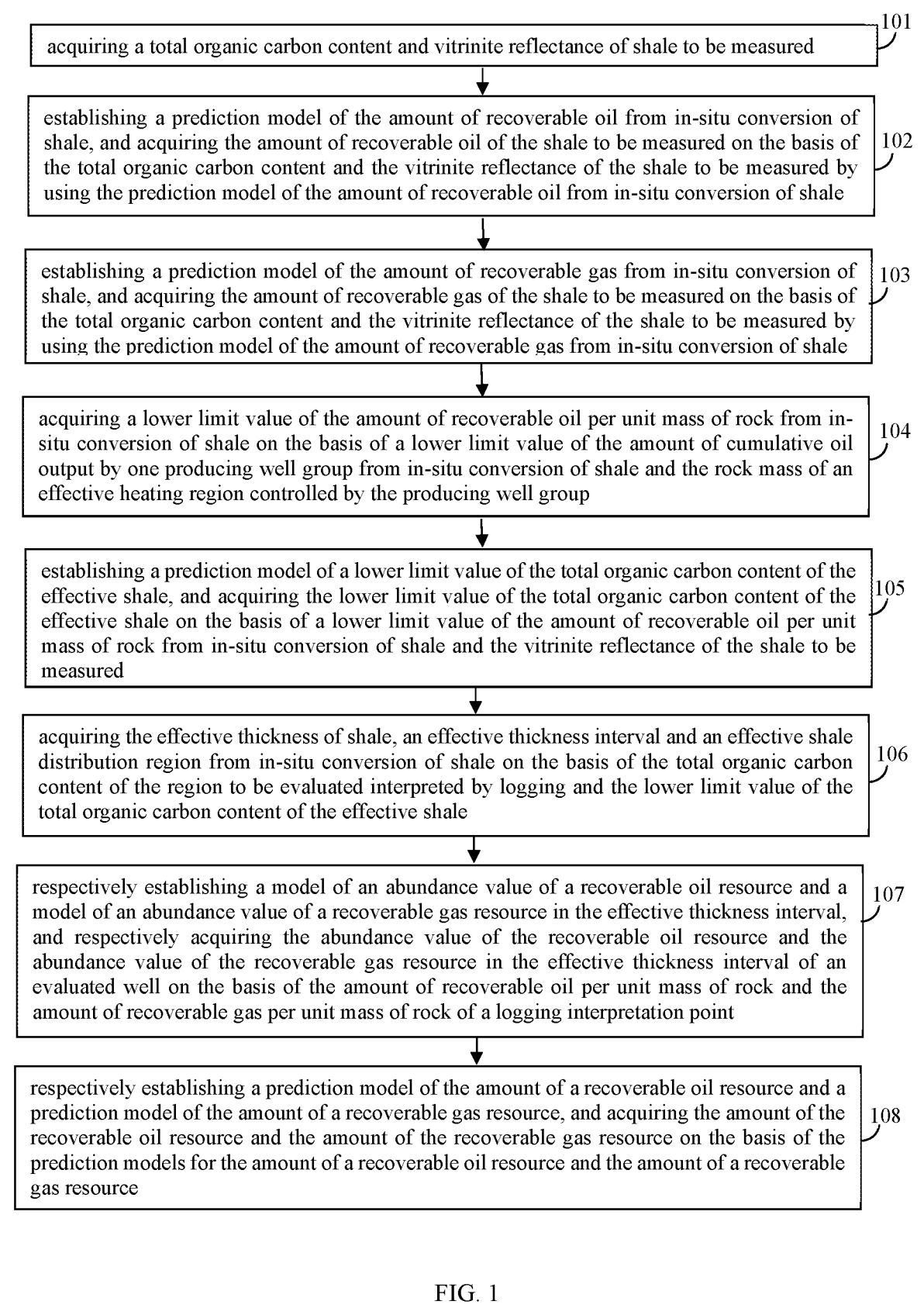

FIG. 1 is a flow diagram of a method for predicting the amount of recoverable oil and gas resources from in-situ conversion of shale provided in an embodiment of the present disclosure, and from FIG. 1, it can be seen that the method includes the following steps:

101: acquiring a total organic carbon content and vitrinite reflectance of shale to be measured;

102: establishing a prediction model of the amount of recoverable oil from in-situ conversion of shale, and acquiring the amount of recoverable oil of the shale to be measured on the basis of the total organic carbon content and the vitrinite reflectance of the shale to be measured by using the prediction model of the amount of recoverable oil from in-situ conversion of shale;

103: establishing a prediction model of the amount of recoverable gas from in-situ conversion of shale, and acquiring the amount of recoverable gas of the shale to be measured on the basis of the total organic carbon content and the vitrinite reflectance of the shale to be measured by using the prediction model of the amount of recoverable gas from in-situ conversion of shale;

104: acquiring a lower limit value of the amount of recoverable oil per unit mass of rock from in-situ conversion of shale on the basis of a lower limit value of the amount of cumulative oil output by one producing well group from in-situ conversion of shale and the rock mass of an effective heating region controlled by the producing well group;

105: establishing a prediction model of a lower limit value of the total organic carbon content of the effective shale, and acquiring the lower limit value of the total organic carbon content of the effective shale on the basis of a lower limit value of the amount of recoverable oil per unit mass of rock from in-situ conversion of shale and the vitrinite reflectance of the shale to be measured;

106: acquiring the effective thickness of shale, an effective thickness interval and an effective shale distribution region from in-situ conversion of shale on the basis of the total organic carbon content of the region to be evaluated interpreted by logging and the lower limit value of the total organic carbon content of the effective shale;

107: respectively establishing a model of an abundance value of a recoverable oil resource and a model of an abundance value of a recoverable gas resource in the effective thickness interval, and respectively acquiring the abundance value of the recoverable oil resource and the abundance value of the recoverable gas resource in the effective thickness interval of an evaluated well on the basis of the amount of recoverable oil per unit mass of rock and the amount of recoverable gas per unit mass of rock of a logging interpretation point; and 108: respectively establishing a prediction model of the amount of a recoverable oil resource and a prediction model of the amount of a recoverable gas resource, and acquiring the amount of the recoverable oil resource and the amount of the recoverable gas resource on the basis of the prediction model of the amount of a recoverable oil resource and the prediction model of the amount of a recoverable gas resource.

The technical solution of the embodiments of the present disclosure achieves the beneficial technical effects as follows.

Firstly, on the basis of the TOC value and the Ro value of the shale to be measured, and the pre-established prediction model of the amount of recoverable oil and prediction model of the amount of recoverable gas from in-situ conversation of shale, the amount of recoverable oil and the amount of recoverable gas of the shale to be measured are obtained, which overcomes the defect that in the prior art, only by acquiring the original HI or original H/C and original TOC of shale and the amount of oil and gas generated by immature shale and the amount of trapped oil and gas, can the amount of recoverable oil and the amount of recoverable gas be established, the defect that precision is low when recovering the original HI or original TOC by using shale that has experienced certain thermal evolution, and the defect that only by obtaining the amount of trapped oil and gas and the amount of generated oil and gas, can the amount of output oil and gas be acquired, and achieves the effect of using the current TOC and Ro of shale in the stratum to obtain the amount of recoverable oil and the amount of recoverable gas from in-situ conversion. Therefore, the present disclosure uses the prediction model of the amount of recoverable oil and the prediction model of the amount of recoverable gas from in-situ conversion of shale, which not only realizes the quantitative prediction of the amount of recoverable oil and gas from in-situ conversion of shale, but also improves the prediction accuracy for the amount of recoverable oil and gas from in-situ conversion of shale.

Secondly, the lower limit value of the amount of recoverable oil per unit mass of rock from in-situ conversion of shale is obtained on the basis of the lower limit value of the amount of cumulative oil output by any producing well group in the same development region from in-situ conversion of shale and the rock mass of an effective heating region controlled by one producing well group, and accordingly, the prediction model of the lower limit value of TOC of the effective shale is established, so as to obtain the lower limit value of TOC of the effective shale, so that the effective thickness of shale, the effective thickness interval and the effective shale distribution region are accurately obtained, which overcomes the defect that the lower limit value of TOC of the effective shale cannot be determined in the prior art, and the defect that the effective thickness of shale, the effective thickness interval and the effective shale distribution region cannot be accurately obtained.

Finally, on the basis of the TOC value of the region to be evaluated interpreted by logging, the rock density value, the measured spacing value, the Ro analysis and assay value (the vitrinite reflectance of a well point in a target stratum) and the effective thickness interval, and the pre-established prediction model of the amount of recoverable oil and prediction model of the amount of recoverable gas, the amount of recoverable oil per unit mass of rock and the amount of recoverable gas per unit mass of rock of the logging interpretation point are obtained; on the basis of the pre-established model of the abundance value of the recoverable oil resource and model of the abundance value of the recoverable gas source, the abundance value of the recoverable oil resource and the abundance value of the recoverable gas source are obtained; on the basis of the effective shale distribution region in the evaluated region, and the pre-established prediction model of the amount of the recoverable oil resource and prediction model of the amount of the recoverable gas resource, the amount of the recoverable oil resource and the amount of the recoverable gas resource are obtained, which overcomes the defect that parameter averages are used to calculate the relevant parameters in the prior art, and the defect of the actual situation that the non-linear relationship between the amount of the recoverable oil and gas resources and TOC cannot be reflected by using the parameter average, and achieves the calculation for different contributions of different TOC points in the longitudinal direction within the effective shale interval to the amount of the recoverable oil and gas resources.

In summary, the technical solution of the embodiment of the present disclosure can quantitatively predict the amount of the recoverable oil and gas resources from in-situ conversion of shale and improve the prediction accuracy and efficiency for the amount of the recoverable oil and gas resources from in-situ conversion of shale.

With reference to FIG. 2 to FIG. 13, all steps of the method for predicting the amount of recoverable oil and gas resources from in-situ conversion of shale provided in the embodiment of the present disclosure are described in detail below.

I. Thermal simulation experiments were carried out on shale samples before establishing all models.

Multiple groups of shale samples in a target stratum of an evaluated region with different TOC values and a Ro value less than 0.5% were collected. In this embodiment, the multiple groups of shale samples are outcrop shale samples collected from the Chang 7 member of the Ordos Basin, and the shale samples with different TOC and Ro less than 0.5% are in 9 groups in total, recorded as No. 1-No. 9, and each group of shale samples were crushed into shale samples of 40-80 meshes, preferably 60 meshes, and completely mixed uniformly; then each group of uniformly mixed shale samples were divided into 11 parts, the mass of each part of shale samples being greater than 3 kg.

The total organic carbon content (TOC) and the vitrinite reflectance (Ro) of each group of shale samples were measured separately and details of experimental data obtained are as shown in Table 1 below.

The TOC of each group of shale samples was measured according to the national standard GB/T 19145-2003 "Determination of Total Organic Carbon in Sedimentary Rock"; Ro was measured according to the industry standard SY/T 5124-2012 "Method for Determining Vitrinite Reflectance in Sedimentary Rock".

250° C. of a simulation temperature, a programmed heating rate of 5° C./d is used; for the second to eleventh preset temperature points, a programmed heating rate of 20° C./d is used until the simulation temperature reaches the temperature of the previous one preset temperature point of a target preset temperature point; when the simulation temperature is between the temperature of the previous one preset temperature point of the target preset temperature point and the temperature of the target preset temperature point, a programmed heating rate of 5° C./d is used; after the simulation temperature reaches the preset temperature, the preset temperature is maintained and the temperature is constant for 10 hours, and so on, thermal simulation of all preset temperature points is completed. The preset pressure for hydrocarbon discharge is 7 MPa and the amount of oil and gas discharged during the thermal simulation is used to calculate the amount of oil and gas output per unit mass of rock.

For each shale sample, thermal simulation experiments of oil and gas output at 11 preset temperatures were respectively carried out. After completing the simulation, the amount of oil output and the amount of gas output per unit mass of rock at a corresponding preset temperature point were obtained on the basis of the ratio of the amount of

TABLE 1

Characteristic parameters of the shale samples in the target stratum of the evaluated region

| Sample number | No. 1 | No. 2 | No. 3 | No. 4 | No. 5 | No. 6 | No. 7 | No. 8 | No. 9 |
|---|---|---|---|---|---|---|---|---|---|
| TOC (wt %) | 0.51 | 2.03 | 3.50 | 5.03 | 6.44 | 8.51 | 13.34 | 20.67 | 25.99 |
| HI (mg/g · TOC) | 388.1 | 423.0 | 494.5 | 487.9 | 498.2 | 498.6 | 503.5 | 541.5 | 531.8 |
| Ro (%) | 0.43 | 0.46 | 0.47 | 0.47 | 0.47 | 0.47 | 0.48 | 0.47 | 0.48 |

The thermal simulation experiments in this embodiment all use a semi-open experimental system with a preset pressure of 5 MPa and different preset temperatures. The thermal simulation experiment specifically includes: loading the shale sample into a reactor and repeatedly compacting the shale sample with 20 MPa pressure, weighing the mass of the shale sample in the reactor before the simulation, and then vacuumizing the reactor and injecting He. There were 11 preset temperature points in the thermal simulation experiment, namely 250° C., 300° C., 320° C., 335° C., 350° C., 360° C., 390° C., 440° C., 500° C., 540° C. and 580° C., and these preset temperatures cover different stages from the beginning to the end of oil and gas generation. For a first preset temperature point at a temperature of 250° C., a programmed heating rate of 20° C./d is used until the simulation temperature is 200° C.; between 200° C. and output oil and the amount of output gas obtained by collection to the mass of the shale sample before the thermal simulation in a corresponding reactor, and experimental data is as shown in Table 2. After the end of the thermal simulation at each preset temperature point, TOC and Ro of residues after extraction were measured, and experimental data is as shown in Table 3.

The TOC of each group of hydrocarbon source rock samples was measured according to the national standard GB/T 19145-2003 "Determination of Total Organic Carbon in Sedimentary Rock"; Ro was measured according to the industry standard SY/T 5124-2012 "Method for Determining Vitrinite Reflectance in Sedimentary Rock".

TABLE 2

Data table of the amount of output oil and the amount of output gas from the thermal simulation experiment on the shale sample in the target stratum of the evaluated region

| | Sample number | | | | | | | | |
|---|---|---|---|---|---|---|---|---|---|
| | No. 1 | | No. 2 | | No. 3 | | No. 4 | | No. 5 |
| Thermal simulation temperature (° C.) | The amount of output oil | The amount of output gas | The amount of output oil | The amount of output gas | The amount of output oil | The amount of output gas | The amount of output oil | The amount of output gas | The amount of output oil |
| 250 | 0.00 | 0.00 | 0.07 | 0.00 | 0.02 | 0.00 | 0.11 | 0.00 | 0.28 |
| 300 | 0.00 | 0.00 | 0.37 | 0.00 | 0.90 | 0.00 | 1.45 | 0.05 | 2.31 |
| 320 | 0.01 | 0.00 | 0.74 | 0.02 | 1.94 | 0.00 | 2.95 | 0.11 | 4.61 |

TABLE 2-continued

Data table of the amount of output oil and the amount of output gas from the thermal simulation experiment on the shale sample in the target stratum of the evaluated region

| 335 | 0.01 | 0.00 | 0.98 | 0.05 | 2.49 | 0.09 | 3.86 | 0.19 | 5.94 |
| 350 | 0.01 | 0.00 | 1.23 | 0.08 | 3.04 | 0.57 | 4.83 | 0.42 | 7.19 |
| 360 | 0.02 | 0.01 | 1.86 | 0.34 | 4.56 | 1.00 | 7.15 | 1.76 | 10.27 |
| 390 | 0.03 | 0.02 | 2.44 | 0.70 | 5.93 | 2.07 | 9.19 | 3.38 | 13.07 |
| 440 | 0.03 | 0.03 | 2.55 | 1.26 | 6.18 | 2.75 | 9.58 | 4.41 | 13.61 |
| 500 | 0.03 | 0.07 | 2.55 | 1.58 | 6.20 | 3.07 | 9.60 | 4.98 | 13.64 |
| 540 | 0.03 | 0.07 | 2.55 | 1.76 | 6.20 | 3.35 | 9.60 | 5.32 | 13.64 |
| 580 | 0.03 | 0.08 | 2.55 | 1.88 | 6.20 | 3.59 | 9.60 | 5.52 | 13.64 |

| | Sample number | | | | | | | | |
| | No. 5 | No. 6 | | No. 7 | | No. 8 | | No. 9 | |
| Thermal simulation temperature (° C.) | The amount of output gas | The amount of output oil | The amount of output gas | The amount of output oil | The amount of output gas | The amount of output oil | The amount of output gas | The amount of output oil | The amount of output gas |
|---|---|---|---|---|---|---|---|---|---|
| 250 | 0.03 | 0.16 | 0.02 | 0.70 | 0.03 | 0.62 | 0.02 | 0.76 | 0.06 |
| 300 | 0.03 | 3.14 | 0.13 | 5.90 | 0.68 | 9.63 | 0.92 | 10.89 | 0.85 |
| 320 | 0.17 | 6.39 | 0.28 | 10.94 | 1.05 | 18.76 | 1.78 | 22.78 | 2.07 |
| 335 | 0.27 | 8.27 | 0.30 | 14.29 | 1.08 | 24.70 | 2.16 | 30.57 | 2.77 |
| 350 | 0.28 | 10.09 | 0.69 | 17.22 | 1.28 | 29.33 | 3.22 | 36.57 | 3.82 |
| 360 | 2.31 | 14.28 | 3.63 | 24.21 | 5.69 | 41.47 | 9.10 | 51.66 | 10.81 |
| 390 | 4.56 | 17.89 | 5.76 | 30.15 | 10.12 | 51.82 | 18.00 | 64.03 | 23.86 |
| 440 | 6.13 | 18.63 | 8.48 | 31.38 | 13.98 | 53.93 | 23.04 | 66.71 | 30.09 |
| 500 | 6.58 | 18.67 | 8.86 | 31.45 | 14.80 | 54.05 | 25.38 | 66.85 | 31.90 |
| 540 | 6.60 | 18.67 | 9.27 | 31.45 | 15.31 | 54.05 | 26.08 | 66.85 | 32.61 |
| 580 | 6.60 | 18.67 | 9.76 | 31.45 | 15.76 | 54.05 | 26.67 | 66.85 | 33.30 |

Note:
The amount of cumulative output oil-mg/g · rock; the amount of cumulative output gas-mL/g · rock.

TABLE 3

TOC and Ro of the residues after extraction from the thermal simulation experiment on the shale sample in the target stratum of the evaluated region

| Thermal simulation temperature (° C.) | Sample number | | | | | | | | | | | | | | | | | | Aver- age |
| | No. 1 | | No. 2 | | No. 3 | | No. 4 | | No. 5 | | No. 6 | | No. 7 | | No. 8 | | No. 9 | | |
| | TOC | Ro | TOC | Ro | TOC | Ro | TOC | Ro | TOC | Ro | TOC | Ro | TOC | Ro | TOC | Ro | TOC | Ro | Ro |
|---|---|---|---|---|---|---|---|---|---|---|---|---|---|---|---|---|---|---|---|
| 250 | 0.51 | 0.57 | 2.02 | 0.55 | 3.47 | 0.59 | 5.02 | 0.56 | 6.43 | 0.59 | 8.45 | 0.59 | 13.25 | 0.58 | 20.54 | 0.57 | 25.82 | 0.60 | 0.58 |
| 300 | 0.48 | 0.78 | 1.87 | 0.72 | 3.18 | 0.76 | 4.63 | 0.78 | 5.85 | 0.72 | 7.75 | 0.78 | 12.11 | 0.75 | 18.92 | 0.79 | 23.54 | 0.75 | 0.76 |
| 320 | 0.44 | 0.80 | 1.73 | 0.88 | 2.96 | 0.81 | 4.24 | 0.84 | 5.44 | 0.84 | 7.21 | 0.84 | 11.17 | 0.85 | 17.32 | 0.84 | 21.27 | 0.82 | 0.84 |
| 335 | 0.37 | 0.95 | 1.39 | 0.93 | 2.37 | 0.88 | 3.44 | 0.88 | 4.37 | 0.92 | 5.80 | 0.90 | 8.99 | 0.91 | 13.48 | 0.93 | 16.98 | 0.89 | 0.91 |
| 350 | 0.31 | 0.98 | 1.18 | 1.00 | 1.97 | 1.03 | 2.88 | 0.99 | 3.68 | 0.96 | 4.78 | 0.97 | 7.48 | 1.01 | 11.51 | 0.99 | 14.38 | 1.02 | 1.00 |
| 360 | 0.30 | 1.09 | 1.12 | 1.10 | 1.76 | 1.09 | 2.56 | 1.03 | 3.23 | 1.07 | 4.45 | 1.10 | 6.80 | 1.03 | 10.29 | 1.06 | 12.60 | 1.05 | 1.07 |
| 390 | 0.33 | 1.26 | 1.30 | 1.23 | 2.11 | 1.21 | 2.97 | 1.22 | 3.78 | 1.28 | 5.01 | 1.29 | 7.64 | 1.24 | 11.75 | 1.23 | 14.84 | 1.22 | 1.24 |
| 440 | 0.37 | 1.68 | 1.37 | 1.70 | 2.20 | 1.67 | 3.14 | 1.63 | 4.00 | 1.65 | 5.22 | 1.70 | 8.16 | 1.68 | 12.12 | 1.68 | 15.07 | 1.67 | 1.67 |
| 500 | 0.38 | 2.41 | 1.41 | 2.41 | 2.25 | 2.41 | 3.20 | 2.41 | 4.12 | 2.37 | 5.38 | 2.34 | 8.21 | 2.30 | 12.18 | 2.27 | 15.17 | 2.30 | 2.36 |
| 540 | 0.38 | 2.88 | 1.40 | 3.00 | 2.20 | 2.94 | 3.29 | 2.88 | 4.14 | 2.94 | 5.41 | 2.97 | 8.22 | 2.94 | 12.26 | 2.94 | 15.28 | 2.88 | 2.93 |
| 580 | 0.38 | 3.76 | 1.39 | 3.76 | 2.26 | 3.72 | 3.25 | 3.76 | 4.16 | 3.76 | 5.47 | 3.68 | 8.34 | 3.76 | 12.29 | 3.61 | 15.32 | 3.65 | 3.72 |

Note:
TOC-wt %; Ro-%.

The average value of Ro after thermal simulation of different shale samples at the same preset temperature in the thermal simulation experiment was obtained to establish the relationship between the simulation temperature of pyrolysis and Ro. The amount of oil and gas output from thermal simulation of shale is related to Ro, in order to facilitate the corresponding study on the degree of thermal evolution of shale under stratigraphic conditions, the simulation temperature is converted into a corresponding Ro value according to the following formula (1):

$$R_o = x_1 e^{x_2 T}; \qquad\qquad \text{formula (1)}$$

in formula (1): Ro is the vitrinite reflectance, %; T is the simulation temperature of pyrolysis, ° C.; $x_1$ and $x_2$ are empirical coefficients, and can be 0.13797 and 0.005667, respectively.

In this embodiment, the relation curve graph between the average value of Ro after thermal simulation of different shale samples under the same preset temperature and the simulation temperature of pyrolysis is as shown in FIG. 2.

II. According to the data obtained during the above thermal simulation experiment, all models are established.

1. According to the data of the amount of output oil obtained from the above thermal simulation experiment and the TOC value and Ro value of the shale samples, an evaluation model of the amount of output oil of different shale under the corresponding TOC and Ro conditions (a prediction model of the amount of recoverable oil from in-situ conversion of shale) is pre-established.

Figure 3:
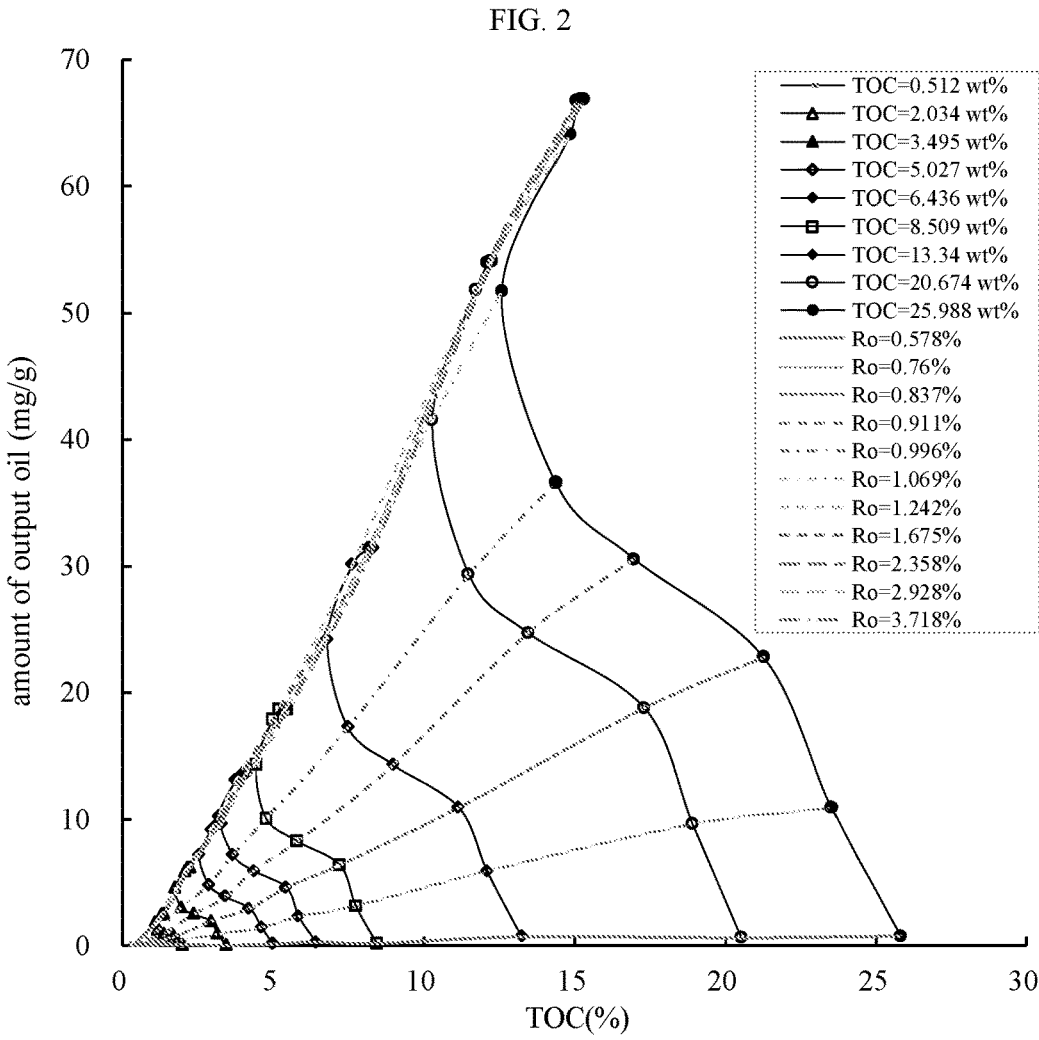
FIG. 3 is a relation diagram of the amount of output oil obtained by thermal simulation and TOC in the embodiment of the present disclosure.

The amount of output oil of shale is related to Ro and TOC of shale. According to the results of the thermal simulation experiments, a relationship model between the amount of output oil and TOC is established. The empirical parameters in the model are extracted to establish a model with Ro. The evaluation model of the amount of output oil as shown in the following formula (2) and FIG. 3 is established.

$$Q_{po} = a_1 \times \left( \left( e^{a_2 Ro + a_3} \right) TOC - e^{a_4 Ro + a_5} \right) + a_6; \qquad \text{formula (2)}$$

wherein Qpo is the amount of remaining output oil per unit mass of shale (to be resolved), mg/g·rock; Ro is the vitrinite reflectance, %; TOC is the organic carbon content, wt %; $a_1$, $a_2$, $a_3$, $a_4$, $a_5$ and $a_6$ are the empirical parameters, and $a_1$ and $a_6$ are 0.99892 and 0.01538 respectively; when Ro≤0.76%, $a_2$ and $a_3$ are 0.4265 and 0.7516 respectively; when 0.76%<Ro≤1.0%, $a_2$ and $a_3$ are −0.4593 and 1.41 respectively; when Ro>0.98%, $a_2$ and $a_3$ are −4.164 and 5.3161 respectively; when Ro≤0.77%, $a_4$ and $a_5$ are 0.068 and 1.1297 respectively; when 0.775%<Ro≤1.06%, $a_4$ and $a_5$ are −2.6881 and 3.2629 respectively, and when Ro>1.06%, $a_4$ and $a_5$ are −3.5488 and 4.1449 respectively.

2. According to the data of the amount of output gas obtained from the above thermal simulation experiment and the TOC value and Ro value of the shale samples, an evaluation model of the amount of output gas of different shale under the corresponding TOC and Ro conditions (a prediction model of the amount of recoverable gas from in-situ conversion of shale) is pre-established.

Figure 4:
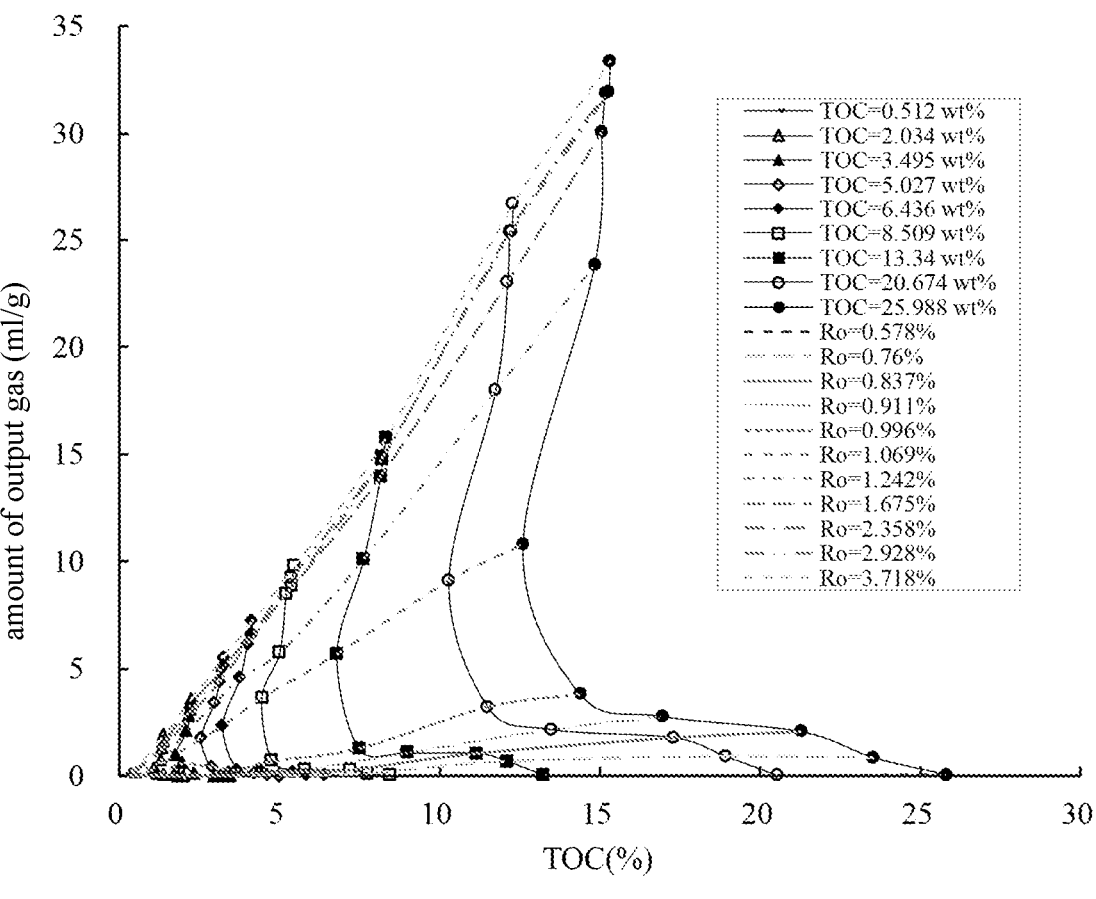
FIG. 4 is a relation diagram of the amount of output gas obtained by thermal simulation and TOC in the embodiment of the present disclosure.

The amount of output gas of shale is related to Ro and TOC of shale. According to the results of the thermal simulation experiments, a relationship model between the amount of output gas and TOC is established. The empirical parameters in the model are extracted to establish a model with Ro. The evaluation model of the amount of output gas as shown in the following formula (3) and FIG. 4 is established.

$$Q_{pg} = \qquad \text{formula (3)}$$

$$b_1 \times \begin{cases} \left( b_2 e^{b_3 Ro} \right) TOC + b_4 \ln Ro + b_5 & Ro \leq 0.84\% \\ \left( b_6 \ln Ro + b_7 \right) TOC + \\ b_8 Ro^2 + b_9 Ro + b_{10} & 0.84\% < Ro \leq 1.07\% \\ \left( b_{11} Ro^{b_{12}} \right) TOC + b_{13} Ro^2 + \\ b_{14} Ro + b_{15} & Ro \geq 1.07\% \end{cases};$$

wherein Qpg is the amount of remaining output gas per unit mass of shale, m³/t·rock; Ro is the vitrinite reflectance, %; TOC is the organic carbon content, wt %; $b_1$, $b_2$, $b_3$, $b_4$, $b_5$, $b_6$, $b_7$, $b_8$, $b_9$, $b_{10}$, $b_{11}$, $b_{12}$, $b_{13}$, $b_{14}$ and $b_{15}$ are the empirical parameters, and are 1.0062, 0.9478, 0.5744, −0.0997, −1.1745, 3.4118, 2.1756, 1.5235, −2.3651, −0.2334, 2.9012, −2.9174, −0.0967, 0.5035 and −0.4776 respectively.

During specific implementation, the solution provided by the embodiment of the present disclosure overcomes the defect in the prior art that only by providing the simulation experiment or providing the original TOC and original HI or original H/C of shale and acquiring the amount of generated oil and gas and the amount of trapped oil and gas, can the amount of output oil and gas be acquired, and the established relations of TOC, Ro and the amount of output oil and gas (the prediction model of the amount of output oil from in-situ conversion of shale and the prediction model of the amount of output gas from in-situ conversion of shale) overcome the defect in the prior art that the amount of output oil and gas of shale with different TOC and Ro cannot be evaluated (predicted), so that the amount of output oil and the amount of output gas of shale with different TOC and Ro values can be correspondingly predicted.

As it takes a long time to simulate the amount of oil and gas output from shale under the in-situ conversation conditions, for regions without thermal simulation experiment data, formulas (3) and (4) can be used to obtain data of the amount of oil and gas output from in-situ conversation of shale in the evaluated region, which is used for the evaluation and optimization of recoverable oil and gas resources and "sweet spot".

III. On the basis of the above-acquired prediction model of the amount of output oil from in-situ conversation of shale and prediction model of the amount of output gas from in-situ conversation of shale, the prediction model of the amount of a recoverable oil resource and the prediction model of the amount of a recoverable gas resource are established.

1. A prediction model of a lower limit value of the amount of recoverable oil per unit mass of rock from in-situ conversation of shale is established.

Figure 5:
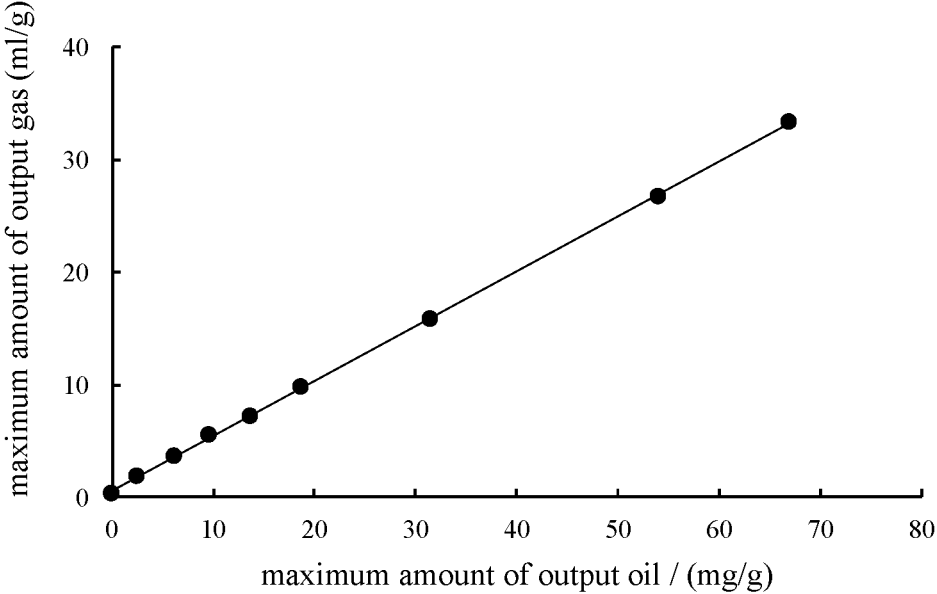
FIG. 5 is a relation diagram of the maximum amount of output gas and the maximum amount of output oil obtained by thermal simulation in the embodiment of the present disclosure.

In the development process of in-situ conversion of shale, in order to develop on an economic scale, the amount of recoverable oil and the amount of recoverable gas per unit mass of shale must be greater than a certain lower limit value. Since there is a very good linear relationship between the maximum amount of recoverable oil and the maximum amount of recoverable gas, it is only needed to determine the lower limit value of recoverable oil. FIG. 5 is a relation diagram of the maximum amount of recoverable oil and the maximum amount of recoverable gas of shale samples from thermal simulation of experiments.

During developing of in-situ conversion of shale on an economic scale, the lower limit value of recoverable oil per unit mass of rock from in-situ conversion of shale is obtained on the basis of a lower limit value of the amount of cumulative oil output by any producing well group in the same development region from in-situ conversion of shale and the rock mass of an effective heating region controlled by the producing well group according to the following formula (4):

$$Q_{po\_limit} = \frac{Q_{oil\_limit}}{Wt_{rock}}; \qquad \text{formula (4)}$$

wherein, $Q_{po\_limt}$ is the lower limit value of the amount of recoverable oil per unit mass of rock from in-situ conversion of shale, mg/g·rock; $Q_{oil\_limt}$ is the lower limit value of the amount of cumulative oil output by one producing well group, mg; $Wt_{rock}$ is the rock mass of the effective heating region controlled by the producing well group, g.

If horizontal wells are used for development, it is assumed that a producing well group includes 10 heating wells and 1 producing well; the heating wells are 15 m apart; the length of the horizontal well is 1200 m; the rock mass in the effective heating region is $708 \times 10^4$ tons. The lower limit value of the amount of oil output by one producing well group is $10 \times 10^4$ tons, and the lower limit value of the amount of recoverable oil per unit mass of rock calculated by the above formula (4) is 14 mg/g·rock.

2. A prediction model of a lower limit value of TOC from in-situ conversation of shale is established.

On the basis of determining the lower limit value of the amount of recoverable oil per unit mass of rock, the lower limit value of TOC from in-situ conversion of shale corresponding to the lower limit value of the amount of recoverable oil per unit mass of rock is derived from formula (2), and the pre-established prediction model of the lower limit value of TOC from in-situ conversion of effective shale is as shown in formula (5) below.

$$TOC_{limt} = \frac{c_1 \times Q_{po\_limt} + e^{c_2 Ro + c_3} + c_4}{e^{c_5 Ro + c_6}}; \qquad \text{formula (5)}$$

wherein, $TOC_{limt}$ is the lower limit value of the total organic carbon content of effective shale, wt %; $Q_{po\_limt}$ is the lower limit value of the amount of recoverable oil per unit mass of rock from in-situ conversion of shale, mg/g·rock; Ro is the vitrinite reflectance of the shale to be tested, %; $c_1$, $c_2$, $c_3$, $c_4$, $c_5$ and $c_6$ are empirical parameters, $c_1$ and $c_4$ are 1.0011 and 0.0154 respectively; when Ro≤0.77%, $c_2$ and $c_3$ are 0.068 and 1.1297 respectively; when 0.775%<Ro≤1.06%, $c_2$ and $c_3$ are −2.6881 and 3.2629 respectively; when Ro>1.06%, $c_2$ and $c_3$ are −3.5488 and 4.1449 respectively; when Ro≤0.76%, $c_5$ and $c_6$ are 0.4265 and 0.7516 respectively; when 0.76%<Ro≤1.0%, $c_5$ and $c_6$ are −0.4593 and 1.41 respectively; when Ro>0.98%, $c_5$ and $c_6$ are −4.164 and 5.3161, respectively.

Figure 6:
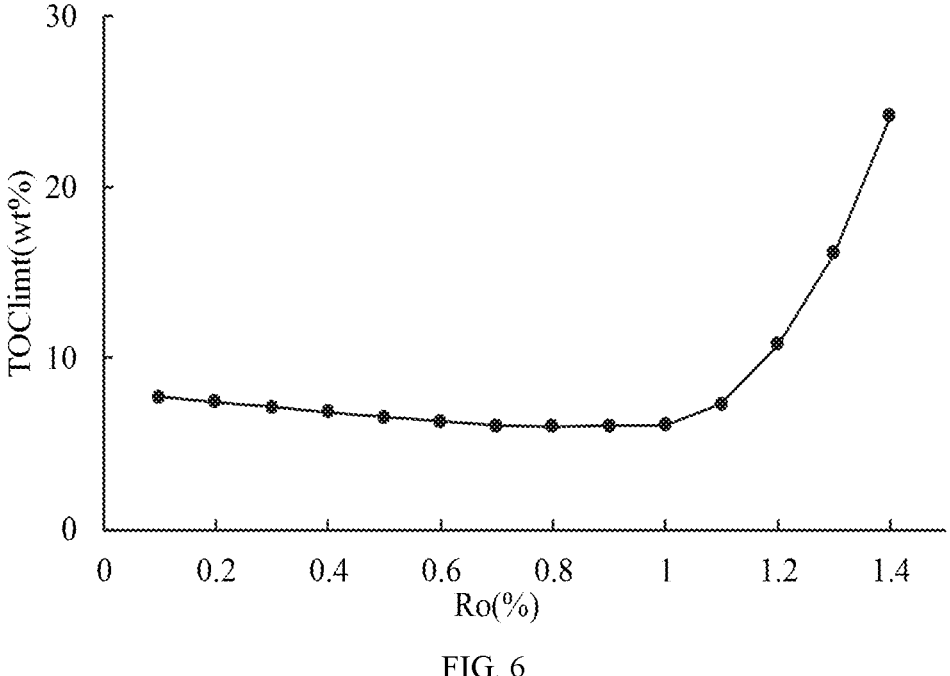
FIG. 6 is a relation diagram of a lower limit value of TOC and Ro when a lower limit value of the amount of oil output per unit of shale is 14 mg/g in the embodiment of the present disclosure.

FIG. 6 is a variation diagram of the lower limit value of the total organic carbon content of the effective shale with Ro calculated by using formula (5) when the lower limit value of the amount of recoverable oil per unit mass of rock is 14 mg/g·rock, and the corresponding lower limit value of the total organic carbon content of the effective shale can be obtained according to different Ro values; when Ro is about 0.8%, the corresponding lower limit value of the total organic carbon content of the effective shale is about 6% at the minimum.

3. The effective thickness of shale, an effective thickness interval and an effective shale distribution region from in-situ conversion of shale are determined.

The effective thickness of shale, the effective thickness interval and the effective shale distribution region from in-situ conversion of shale are determined by using the lower limit value of the total organic carbon content of the effective shale and TOC interpreted by logging and the vitrinite reflectance according to the following rules.

When the continuous thickness of shale with the total organic carbon content interpreted by logging greater than the lower limit value of the total organic carbon content of the effective shale is greater than a set value of 1-15 m, the set value of 5 m is used as the apparent effective thickness of shale, and a depth interval corresponding to the apparent effective thickness of shale is an apparent effective thickness interval; between two adjacent apparent effective thickness intervals, when the continuous thickness of shale with the total organic carbon content interpreted by logging less than the lower limit value of the total organic carbon content of the effective shale is less than a set value of 0.5-5 m, the set value is determined as 2 m, and this interval is calculated into the apparent effective thickness of shale; when the continuous thickness of shale with the total organic carbon content interpreted by logging less than the lower limit value of the total organic carbon content of the effective shale is greater than a set value of 0.5-5 m, the set value is determined as 2 m, and this interval is not calculated into the apparent effective thickness of shale.

When the apparent effective thickness of shale is greater than a set value of 3-15 m, the set value of 5 m is used as the apparent effective thickness of shale, the apparent effective thickness of shale is the effective thickness of shale, and an interval corresponding to the top and bottom of the effective thickness of shale is the effective thickness interval.

When the apparent effective thickness of shale is less than or equal to a set value of 3-15 m, the set value of 5 m is used as the apparent effective thickness of shale, however, the apparent effective thickness of shale cannot be used as the effective thickness of shale and thus cannot be used as an independently developed interval, and the amount of recoverable resources is not calculated for this interval; when the longitudinal distance between two or more effective thickness intervals exceeds a preset thickness value of 0.5-5 m (preferably 3 m), each effective thickness interval will be treated separately as a separate effective thickness interval of shale, i.e., treated as an independent series of development strata.

On the basis of the effective thickness of shale at well points in the evaluated region, the effective thickness distribution of shale in the evaluated region is obtained with a non-equidistant interpolation method such as a three-point method, a five-point method, a finite element method, a Kriging method, a linear interpolation method and a non-linear interpolation method, wherein the grid spacing of the non-equidistant interpolation method uses a preset value of 0.1-10 km (for example, 2 km), when the effective thickness of shale in the evaluated region is greater than a preset value of 3-15 m of the effective thickness, 5 m is used as the boundary of the effective thickness distribution region of shale, and the region where the effective thickness of shale is greater than 5 m is the effective shale distribution region.

Figure 7:
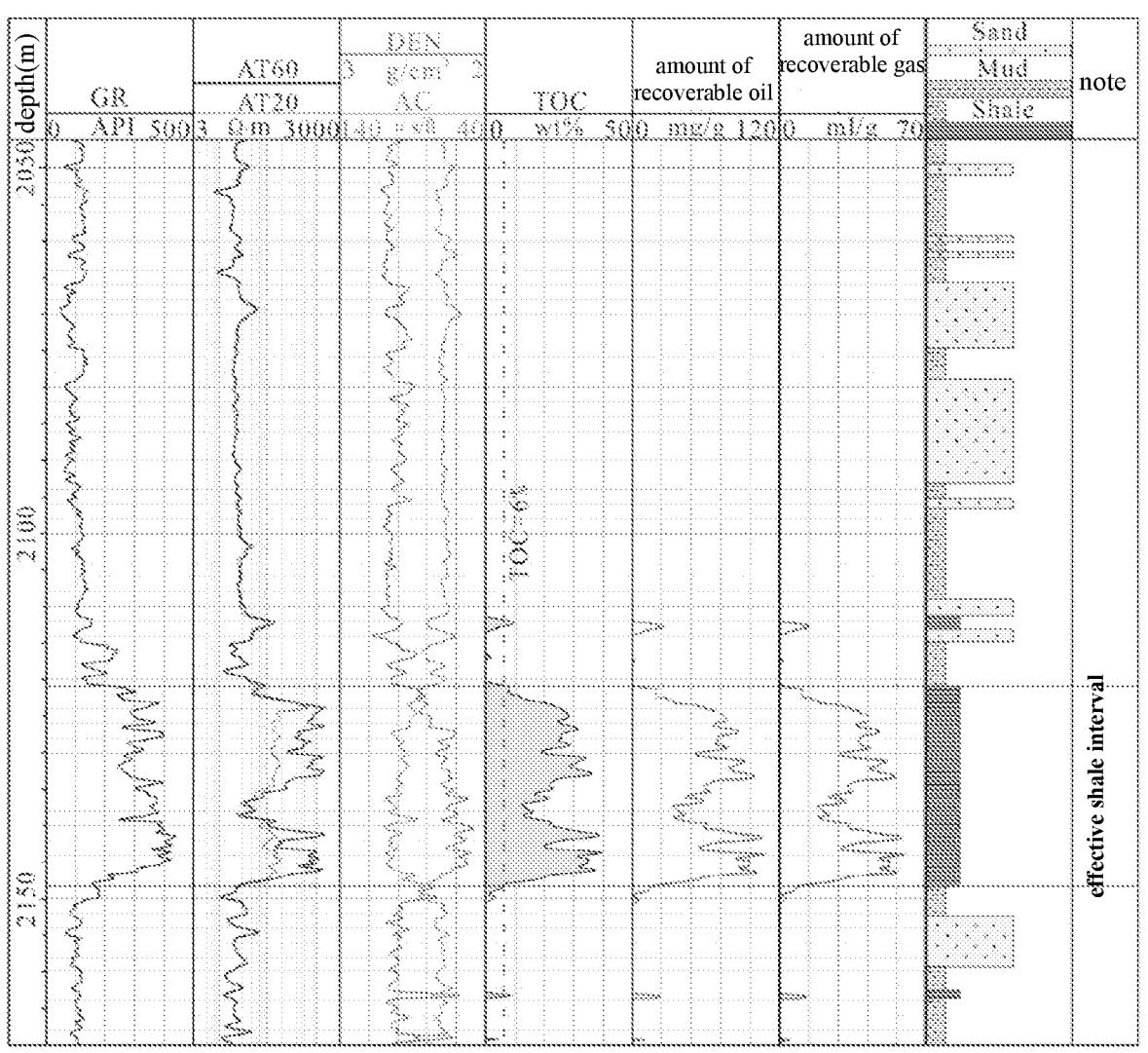
FIG. 7 is a schematic diagram when no interlayer exists in an effective shale interval in the embodiment of the present disclosure.
Figure 8:
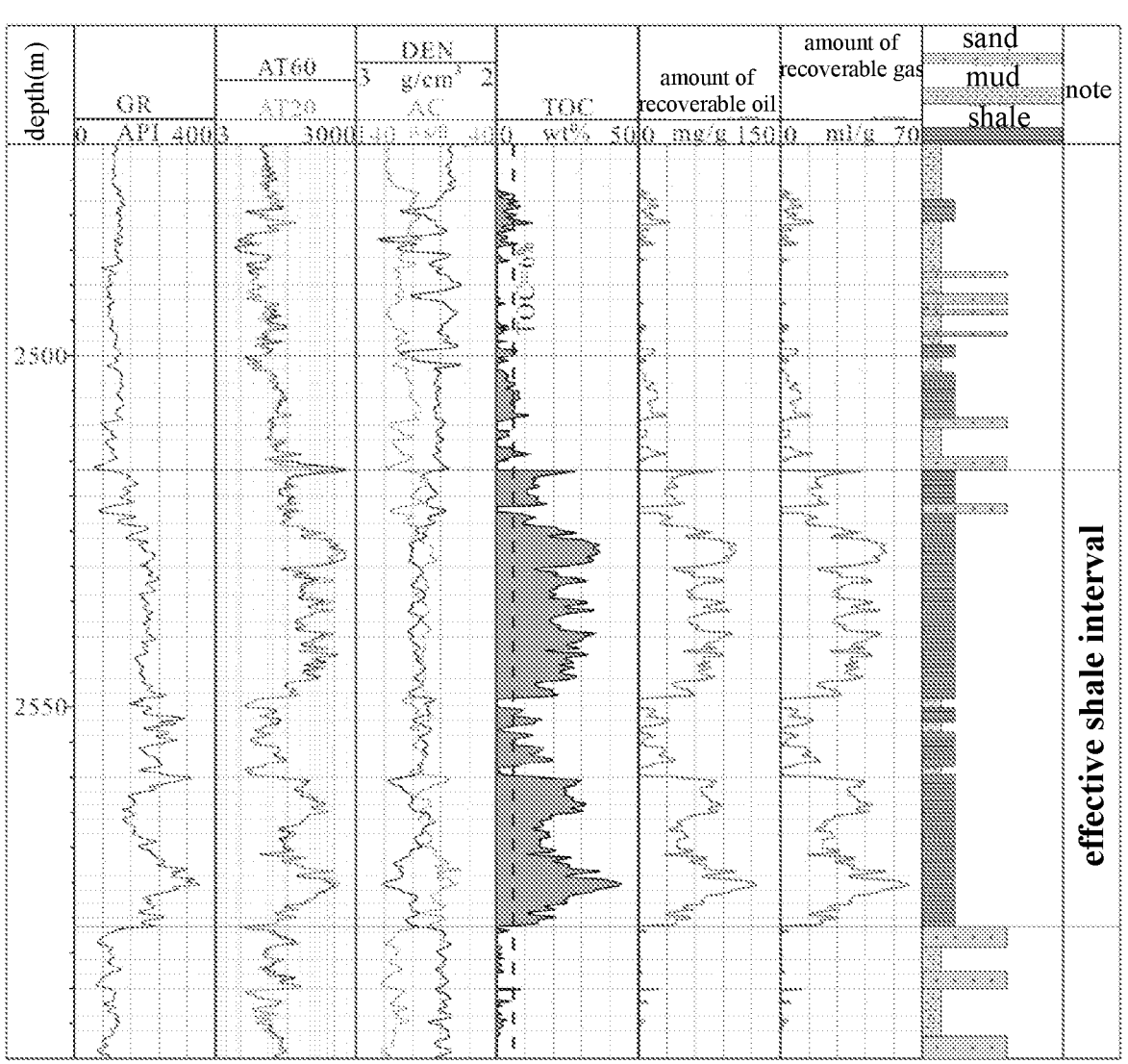
FIG. 8 is a schematic diagram when an interlayer exists in the effective shale interval in the embodiment of the present disclosure.

FIG. 7 is a schematic diagram when no interlayer exists in the effective shale interval, and FIG. 8 is a schematic diagram when an interlayer exists in the effective shale interval.

4. Predicting models of the amount of recoverable oil and gas resources from in-situ conversion of shale are established.

On the basis of TOC interpreted by logging, the TOC value of a logging interpretation point in the effective shale interval, a rock density value and a measured spacing value are acquired; on the basis of the Ro value of a well point in a target stratum acquired by analysis and assay, the amount of recoverable oil per unit mass of rock and the amount of recoverable gas per unit mass of rock of the logging interpretation point are acquired by using the pre-established prediction model of the amount of recoverable oil and prediction model of the amount of recoverable gas.

An abundance value of a recoverable oil resource and an abundance value of a recoverable gas resource in the effective shale interval of the evaluated well are respectively acquired according to the models as shown in the following formulas (6) and (7).

$$AOR = 10^{13} \times \sum_{i=1}^{n} (Q_{po\_i} \times L_{inter} \times \rho_i); \qquad \text{formula (6)}$$

$$AGR = 10^{14} \times \sum_{i=1}^{n} (Q_{pg\_i} \times L_{inter} \times \rho_i); \qquad \text{formula (7)}$$

wherein, AOR is the abundance of the recoverable oil resource of an evaluated region, 10,000 tons/km$^2$; AGR is the abundance of the recoverable gas resource of the evaluated region, 100 million cubic meters/km$^2$; $Q_{po\_i}$ is the amount of recoverable oil per unit mass of rock of an ith logging point in the effective interval, mg/g·rock; $Q_{pg\_i}$ is the amount of recoverable gas per unit mass of rock of the ith logging point in the effective interval, m$^3$/t·rock; $\rho_i$ is the rock density value of the ith logging point in the effective interval, g/cm$^3$; $L_{inter}$ is the logging spacing of the evaluated well, m; n is the total number of logging points in the effective interval, and n is an integer.

On the basis of the abundance values of the recoverable oil resources and the abundance values of the recoverable gas resources for all the well points in the evaluated region, planar distribution of the abundance of the recoverable oil resource and the abundance of the recoverable gas resource in the evaluated region can be obtained by using the non-equidistant interpolation methods such as the three-point method, the five-point method, the finite element method, the Kriging method, the linear interpolation method and the non-linear interpolation method, the spacing of interpolation grids uses a preset value of 0.1-10 km, for example 2 km.

On the basis of the area of the effective shale distribution region in the evaluated region, the amount of the recoverable oil resource and the amount of the recoverable gas resource in the effective shale distribution region of the evaluated region are respectively acquired by using the models as shown in formula (8) and formula (9).

$$NO = \sum_{j=1}^{m} (AOR_j \times A_j); \qquad \text{formula (8)}$$

$$NG = \sum_{j=1}^{m} (AGR_j \times A_j); \qquad \text{formula (9)}$$

wherein NO is the amount of the recoverable oil resource in the evaluated region, 10,000 tons; NG is the amount of the recoverable gas resource in the evaluated region, 100 million cubic meters; $AOR_j$ is the abundance of the recoverable oil resource of a jth grid in the effective shale distribution region, 10,000 tons/km$^2$; $AGR_j$ is the abundance of the recoverable gas resource of the jth grid in the effective shale distribution region, 100 million cubic meters/km$^2$; $A_j$ is the area of the jth grid in the effective shale distribution region, km$^2$; m is the number of grids in the effective shale distribution region, and m is an integer.

Figure 9:
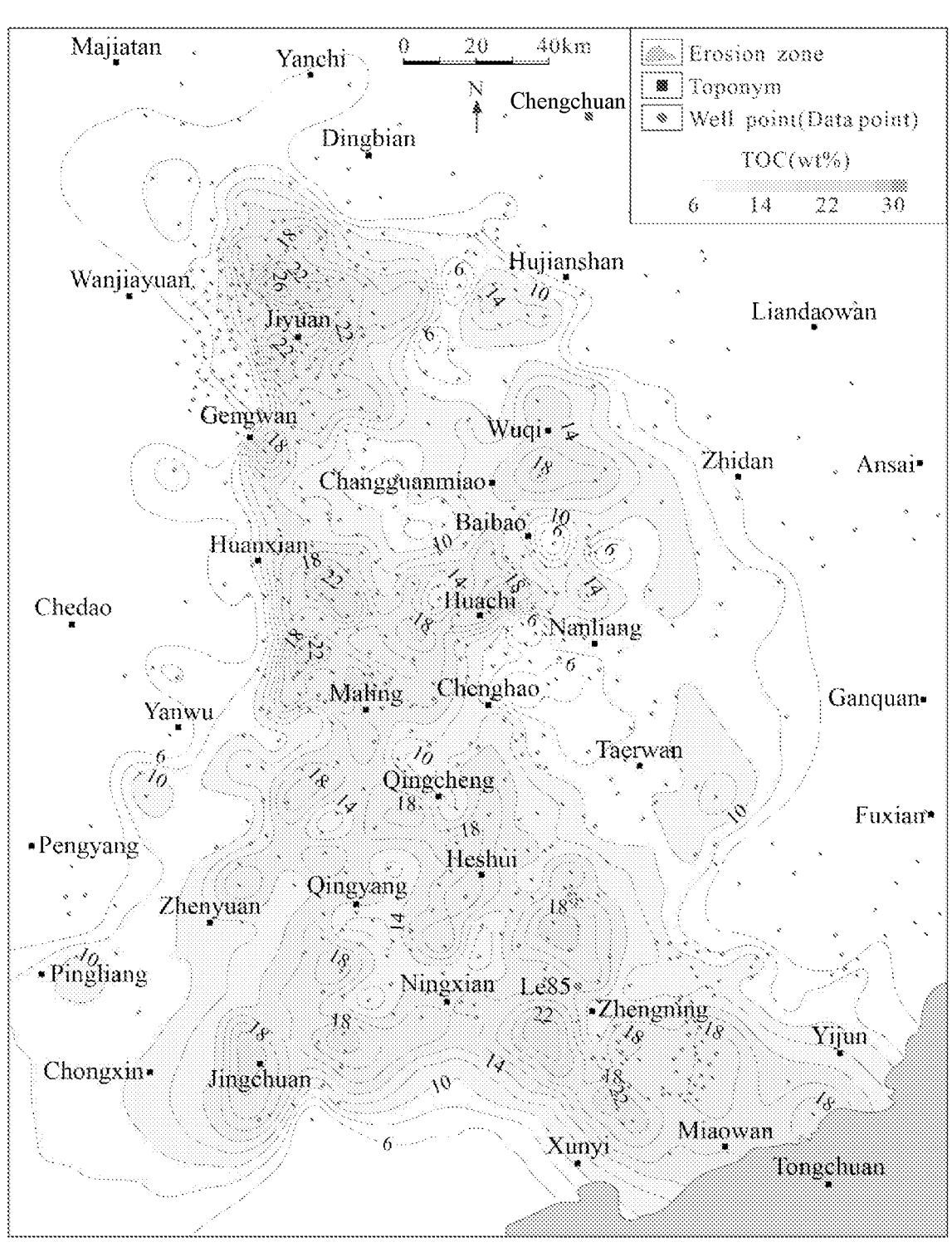
FIG. 9 is a distribution diagram of TOC of shale in the Chang $7_3$ sub-member of the Ordos Basin in the embodiment of the present disclosure.

FIG. 9 is a distribution diagram of TOC with TOC greater than TOC$_{limt}$ obtained by using TOC interpreted by logging for shale of the Chang $7_3$ sub-member of the Ordos Basin. FIG. 9 represents a distribution region that can be subjected to mining from in-situ conversation from the perspective of TOC, and the higher the TOC, the greater the potential of in-situ conversation.

Figure 10:
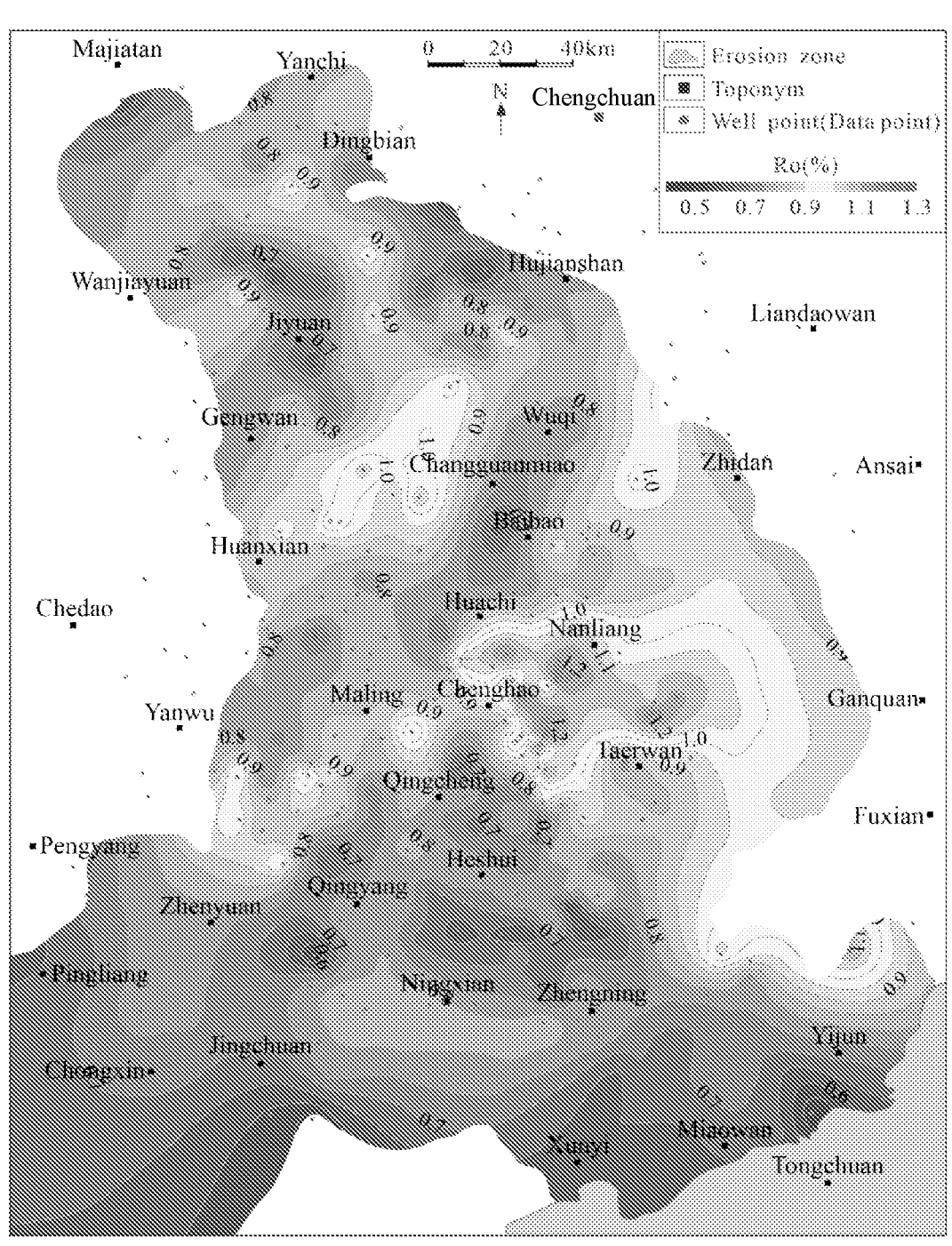
FIG. 10 is a distribution diagram of Ro of shale in the Chang $7_3$ sub-member of the Ordos Basin in the embodiment of the present disclosure.

FIG. 10 is a distribution diagram of Ro obtained from core analysis for shale of the Chang $7_3$ sub-member of the Ordos Basin. From FIG. 9, we can see the maturity of shale suitable for mining from in-situ conversation and the potential of in-situ conversion of the shale. The smaller the Ro, the greater the potential of in-situ conversion.

Figure 11:
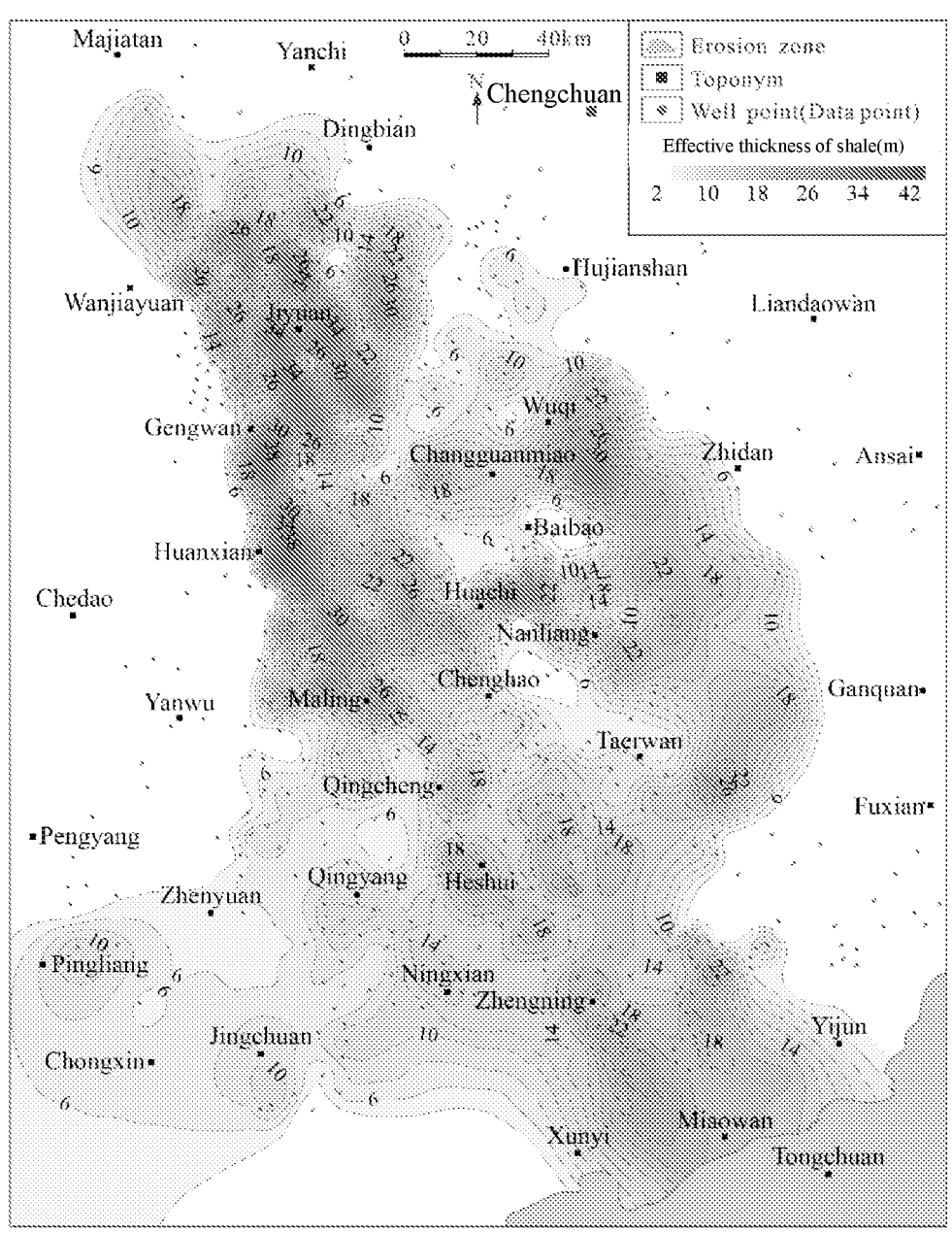
FIG. 11 is a distribution diagram of an effective thickness of shale in the Chang $7_3$ sub-member of the Ordos Basin in the embodiment of the present disclosure.

FIG. 11 is a distribution diagram of an effective thickness of shale obtained by using the method provided by the embodiment of the present disclosure for shale of the Chang $7_3$ sub-member of the Ordos Basin, wherein the greater the effective thickness of shale, the greater the potential of in-situ conversion.

Figure 12:
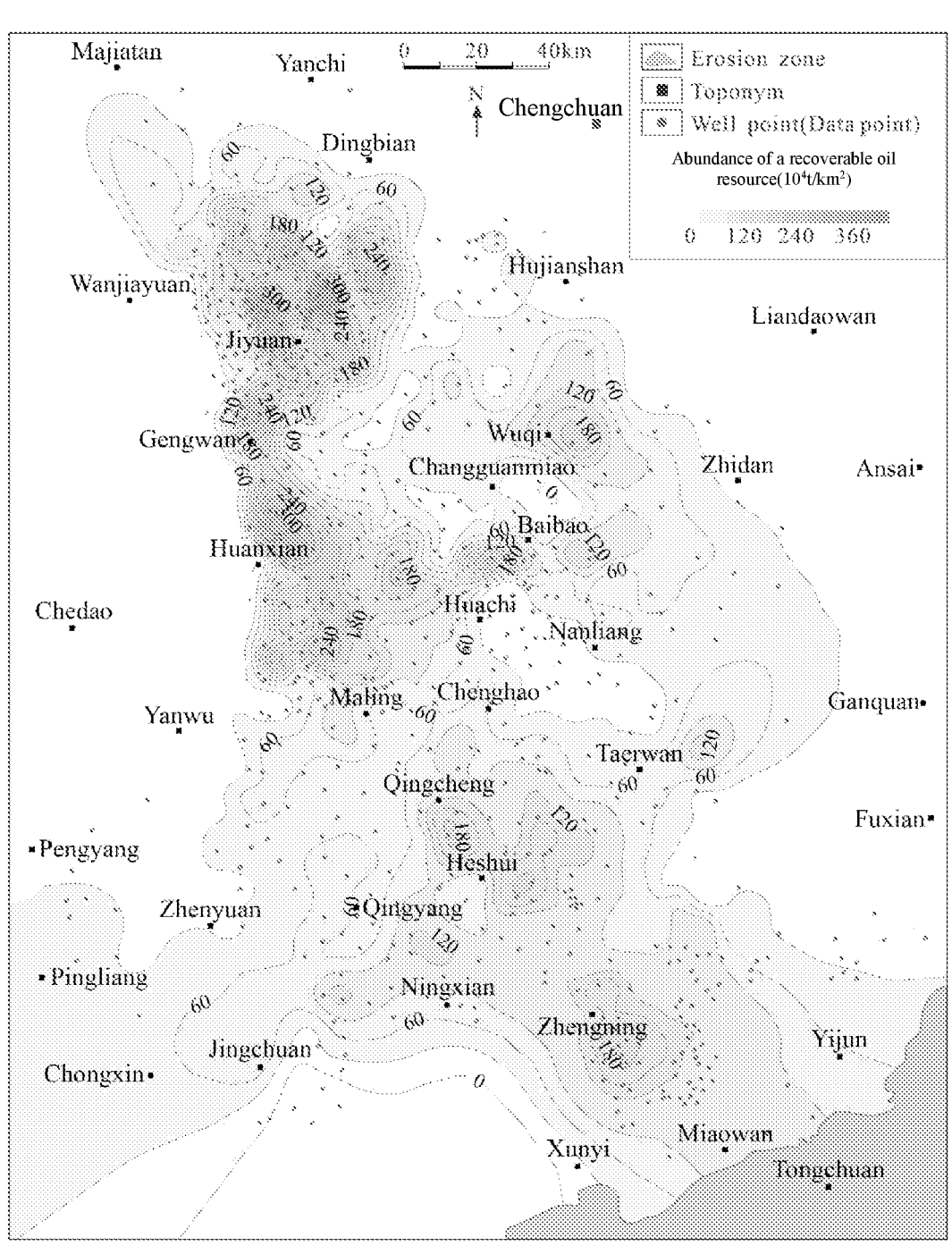
FIG. 12 is a distribution diagram of the abundance of a recoverable oil resource of shale in the Chang $7_3$ sub-member of the Ordos Basin in the embodiment of the present disclosure.

FIG. 12 is a distribution diagram of the abundance of a recoverable oil resource in an effective thickness distribution range of shale obtained by using the method provided by the embodiment of the present disclosure for shale of the Chang $7_3$ sub-member of the Ordos Basin, wherein the greater the abundance of the recoverable oil resource, the greater the recoverable oil resource from in-situ conversation per unit area of shale, and the more favorable development of in-situ conversion.

Figure 13:
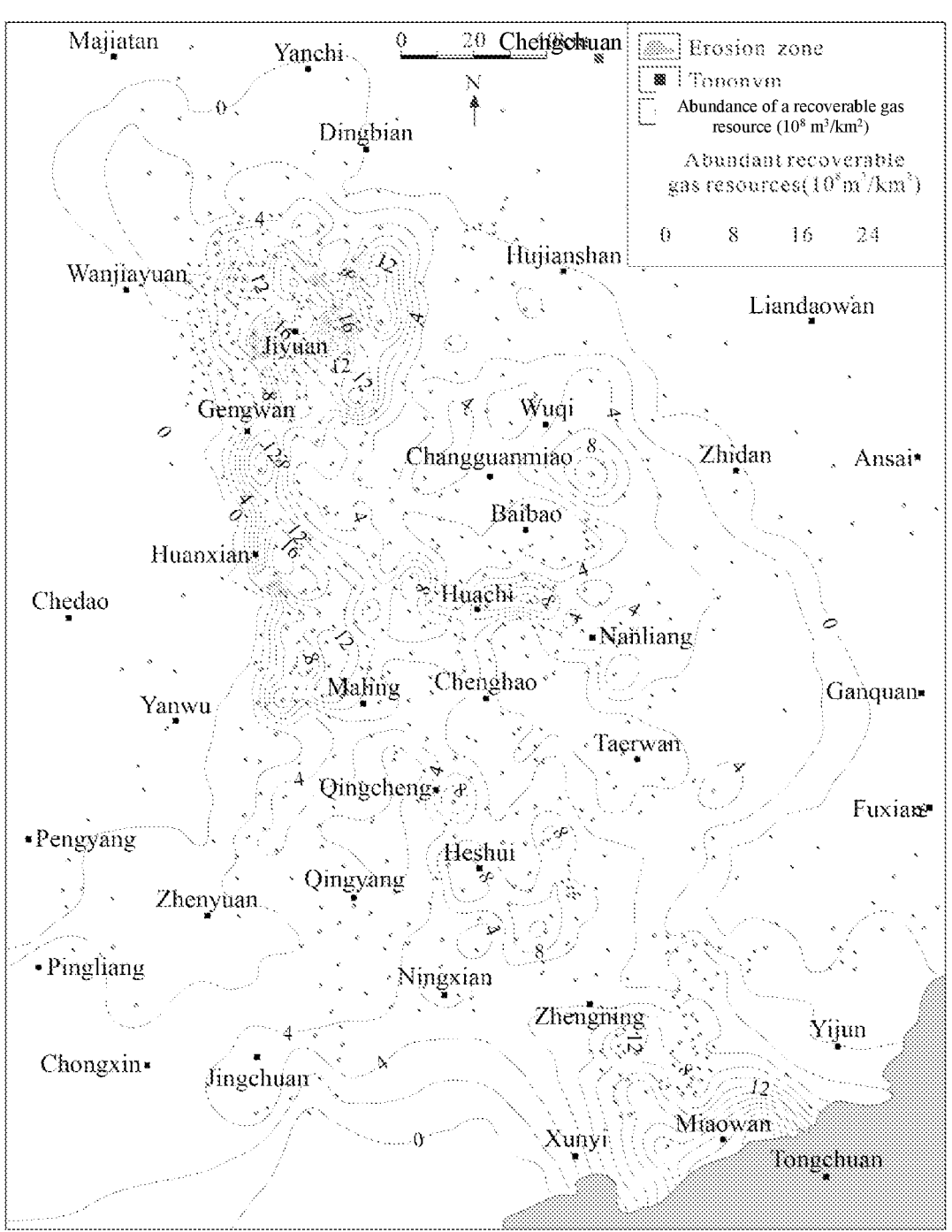
FIG. 13 is a distribution diagram of the abundance of a recoverable gas resource of shale in the Chang $7_3$ sub-member of the Ordos Basin in the embodiment of the present disclosure.

FIG. 13 is a distribution diagram of abundance of a recoverable gas resource obtained by using the method provided by the embodiment of the present disclosure for shale of the Chang $7_3$ sub-member of the Ordos Basin, wherein the greater the abundance of the recoverable gas resource, the greater the recoverable gas resource from in-situ conversation per unit area of shale, the more favorable development of in-situ conversion.

The amount of the recoverable oil resource from in-situ conversation of the shale of the Chang $7_3$ sub-member of the Ordos Basin obtained by using the method provided by the embodiment of the present disclosure is 45.2 billion tons, and the amount of the recoverable gas resource is 37 trillion cubic meters.

During specific implementation, the technical solution of the embodiment of the present disclosure can quantitatively evaluate the amount of the recoverable oil resource and the amount of the recoverable gas resource from in-situ conversion of shale with different TOC and Ro.

Figure 14:
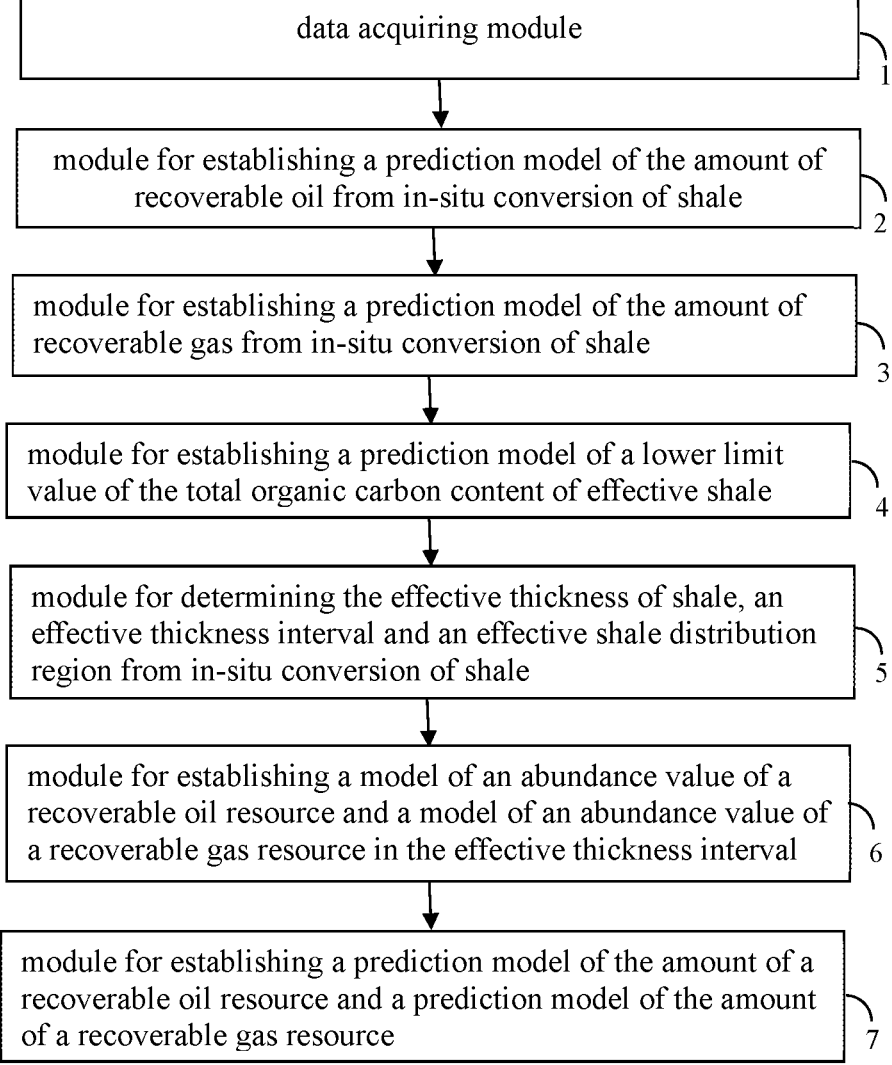
FIG. 14 is a structural schematic diagram of an apparatus for predicting the amount of recoverable oil and gas resources from in-situ conversion of shale provided by an embodiment of the present disclosure.

Based on the same disclosure concept, an embodiment of the present disclosure further provides an apparatus for predicting the amount of recoverable oil and gas resources from in-situ conversion of shale, since the principle of the apparatus for solving the problems is similar with that of the method for predicting the amount of recoverable oil and gas resources from in-situ conversion of shale, the implementation of the apparatus can refer to the implementation of the method, and the same description will not be repeated. FIG. 14 is a structural schematic diagram of an apparatus for predicting the amount of recoverable oil and gas resources from in-situ conversion of shale provided by the embodiment of the present disclosure. As shown in FIG. 14, the apparatus for predicting the amount of recoverable oil and gas resources from in-situ conversion of shale includes:

a data acquiring module 1, used for acquiring a total organic carbon content and vitrinite reflectance of shale to be measured in a region to be evaluated;

a module 2 for establishing a prediction model of the amount of recoverable oil from in-situ conversion of shale, used for establishing the prediction model of the amount of recoverable oil from in-situ conversion of shale, and acquiring the amount of recoverable oil of the shale to be measured on the basis of the total organic carbon content and the vitrinite reflectance of the shale to be measured by using the prediction model of the amount of recoverable oil from in-situ conversion of shale;

a module 3 for establishing a prediction model of the amount of recoverable gas from in-situ conversion of shale, used for establishing the prediction model of the amount of recoverable gas from in-situ conversion of shale, and acquiring the amount of recoverable gas of the shale to be measured on the basis of the total organic carbon content and the vitrinite reflectance of the shale to be measured by using the prediction model of the amount of recoverable gas from in-situ conversion of shale;

a module 4 for establishing a prediction model of a lower limit value of the total organic carbon content of the effective shale, used for establishing the prediction model of the lower limit value of the total organic carbon content of the effective shale, and acquiring the lower limit value of the total organic carbon content of the effective shale on the basis of the lower limit value of the amount of recoverable oil per unit mass of rock from in-situ conversion of shale and the vitrinite reflectance of the shale to be measured;

a module 5 for determining the effective thickness of shale, an effective thickness interval and an effective shale distribution region from in-situ conversion of shale, used for determining the effective thickness of shale, the effective thickness interval and the effective shale distribution region from in-situ conversion of shale on the basis of the total organic carbon content of the region to be evaluated interpreted by logging and the lower limit value of the total organic carbon content of the effective shale;

a module 6 for establishing a model of an abundance value of a recoverable oil resource and a model of an abundance value of a recoverable gas resource in the effective thickness interval, used for respectively establishing the model of the abundance value of the recoverable oil resource and the model of the abundance value of the recoverable gas resource in the effective thickness interval, and respectively acquiring the abundance value of the recoverable oil resource and the abundance value of the recoverable gas resource in the effective thickness interval of an evaluated well on the basis of the amount of recoverable oil per unit mass of rock and the amount of recoverable gas per unit mass of rock of a logging interpretation point; and a module 7 for establishing a prediction model of the amount of a recoverable oil resource and a prediction model of the amount of a recoverable gas resource, used for respectively establishing the prediction model of the amount of the recoverable oil resource and the prediction model of the amount of the recoverable gas resource, and acquiring the amount of the recoverable oil resource and the amount of the recoverable gas resource on the basis of the prediction model of the amount of the recoverable oil resource and the prediction model of the amount of the recoverable gas resource.

In one embodiment, the module for establishing a prediction model of the amount of recoverable oil from in-situ conversion of shale is specifically used for, establishing a relationship model between the amount of output oil and the total organic carbon content on the basis of data of the amount of output oil acquired by performing thermal simulation experiments on a plurality of different shale samples, and the total organic carbon content and the vitrinite reflectance of the shale samples, and then extracting empirical parameters in the model to establish a model with the vitrinite reflectance, so as to establish the prediction model of the amount of recoverable oil from in-situ conversion of shale.

In one embodiment, the module for establishing a prediction model for the amount of recoverable oil from in-situ conversion of shale is further used for establishing the prediction model of the amount of recoverable oil from in-situ conversion of shale according to the following formula:

$$Q_{po} = a_1 \times \left( \left( e^{a_2 Ro + a_3} \right) TOC - e^{a_4 Ro + a_5} \right) + a_6;$$

wherein, $Q_{po}$ is the amount of recoverable oil of the shale to be measured, mg/g·rock; Ro is the vitrinite reflectance of the shale to be measured, %; TOC is the total organic carbon content of the shale to be measured, wt %; $a_1$, $a_2$, $a_3$, $a_4$, $a_5$ and $a_6$ are the empirical parameters.

In one embodiment, the module for establishing a prediction model of the amount of recoverable gas from in-situ conversion of shale is specifically used for, establishing a relationship model between the amount of output gas and the total organic carbon content on the basis of data of the amount of output gas acquired by performing thermal simulation experiments on a plurality of different shale samples, and the total organic carbon content and the vitrinite reflectance of the shale samples, and then extracting empirical parameters in the model to establish a model with the vitrinite reflectance, so as to establish the prediction model of the amount of recoverable gas from in-situ conversion of shale.

In one embodiment, the module for establishing a prediction model of the amount of recoverable gas from in-situ conversion of shale is further used for establishing the prediction model of the amount of recoverable gas from in-situ conversion of shale according to the following formula:

$$Q_{pg} = b_1 \times \begin{cases} \left( b_2 e^{b_3 Ro} \right) TOC + b_4 \ln Ro + b_5 & Ro \leq w_1 \\ \left( b_6 \ln Ro + b_7 \right) TOC + b_8 Ro^2 + b_9 Ro + b_{10} & w_1 < Ro \leq w_2 ; \\ \left( b_{11} Ro^{b_{12}} \right) TOC + b_{13} Ro^2 + b_{14} Ro + b_{15} & Ro \geq w_2 \end{cases}$$

wherein, $Q_{pg}$ is the amount of recoverable gas of the shale to be measured, m³/t·rock; Ro is the vitrinite reflectance of the shale to be measured, %; TOC is the total organic carbon content of the shale to be measured, wt %; $b_1$, $b_2$, $b_3$, $b_4$, $b_5$, $b_6$, $b_7$, $b_8$, $b_9$, $b_{10}$, $b_{11}$, $b_{12}$, $b_{13}$, $b_{14}$ and $b_{15}$ are the empirical parameters; $w_1$ is 0.5%-1.0%, and $w_2$ is 1.0%-1.4%.

In one embodiment, the module for establishing a prediction model of a lower limit value of the total organic carbon content of effective shale includes a unit for acquiring a lower limit value of the amount of recoverable oil per unit mass of rock from in-situ conversion of shale, used for acquiring the lower limit value of the amount of recoverable oil per unit mass of rock from in-situ conversion of shale on the basis of a lower limit value of the amount of cumulative oil output by any producing well group in the same development region from in-situ conversion of shale and the rock mass of an effective heating region controlled by the producing well group according to the following formula:

$$Q_{po\_limt} = \frac{Q_{oil\_limt}}{Wt_{rock}};$$

wherein, $Q_{po\_limt}$ is the lower limit value of the amount of recoverable oil per unit mass of rock from in-situ conversion of shale, mg/g·rock; $Q_{oil\_limt}$ is the lower limit value of the amount of cumulative oil output by one producing well group from in-situ conversion of shale, mg; $Wt_{rock}$ is the rock mass of the effective heating region controlled by the producing well group from in-situ conversion of shale, g.

In one embodiment, the module for establishing a prediction model of a lower limit value of the total organic carbon content of effective shale is specifically used for establishing the prediction model of the lower limit value of the total organic carbon content of the effective shale on the basis of the prediction model of the amount of recoverable oil from in-situ conversion of shale and the lower limit value of the amount of recoverable oil per unit mass of rock from in-situ conversion of shale according to the following formula:

$$TOC_{limt} = \frac{c_1 \times Q_{po\_limt} + e^{c_2 Ro + c_3} + c_4}{e^{c_5 Ro + c_6}};$$

wherein $TOC_{limt}$ is the lower limit value of the total organic carbon content of the effective shale, wt %; $Q_{po\_limt}$ is the lower limit value of the amount of recoverable oil per unit mass of rock from in-situ conversion of shale, mg/g·rock; Ro is the vitrinite reflectance of the shale to be measured, %; $c_1$, $c_2$, $c_3$, $c_4$, $c_5$ and $c_6$ are empirical parameters.

In one embodiment, the module for determining the effective thickness of shale, an effective thickness interval and an effective shale distribution region from in-situ conversion of shale is specifically used for determining the effective thickness of shale, the effective thickness interval and the effective shale distribution region from in-situ conversion of shale on the basis of the total organic carbon content of the region to be evaluated interpreted by logging and the lower limit value of the total organic carbon content of the effective shale according to the following rules:

when the continuous thickness of shale with the total organic carbon content interpreted by logging greater than the lower limit value of the total organic carbon content of the effective shale is greater than a set value of 1-15 m, the set value of 5 m is used as the apparent effective thickness of shale, and a depth interval corresponding to the apparent effective thickness of shale is an apparent effective thickness interval; between two adjacent apparent effective thickness intervals, when the continuous thickness of shale with the total organic carbon content interpreted by logging less than the lower limit value of the total organic carbon content of the effective shale is less than a set value of 0.5-5 m, the set value is determined as 2 m, and this interval is calculated into the apparent effective thickness of shale; when the continuous thickness of shale with the total organic carbon content interpreted by logging less than the lower limit value of the total organic carbon content of the effective shale is greater than a set value of 0.5-5 m, the set value is determined as 2 m, and this interval is not calculated into the apparent effective thickness of shale;

when the apparent effective thickness of shale is greater than a set value of 3-15 m, the set value of 5 m is used as the apparent effective thickness of shale, the apparent effective thickness of shale is the effective thickness of shale, and an interval corresponding to the top and bottom of the effective thickness of shale is the effective thickness interval;

when the apparent effective thickness of shale is less than or equal to a set value of 3-15 m, the set value of 5 m is used as the apparent effective thickness of shale, however, the apparent effective thickness of shale cannot be used as the effective thickness of shale and thus cannot be used as an independently developed interval, and the amount of a recoverable resource is not calculated for this interval; when the longitudinal distance between two or more effective thickness intervals exceeds a preset thickness value of 0.5-5 m, each effective thickness interval will be treated separately as a separate effective thickness interval of shale, i.e., treated as an independent series of development strata;

obtaining the effective thickness distribution of shale in the evaluated region with a non-equidistant interpolation method on the basis of the effective thickness of shale at well points in an evaluated region, wherein the grid spacing of the non-equidistant interpolation method uses a preset value of 0.1-10 km, and when the effective thickness of shale in the evaluated region is greater than a preset value of 3-15 m of the effective thickness, 5 m is used as the boundary of the effective thickness distribution region of shale, and the region where the effective thickness of shale is greater than 5 m is the effective shale distribution region.

In one embodiment, the module for establishing a model of an abundance value of a recoverable oil resource and a model of an abundance value of a recoverable gas resource in the effective thickness interval is specifically used for, respectively establishing the model of the abundance value of the recoverable oil resource and the model of the abundance value of the recoverable gas resource in the effective shale interval according to the amount of recoverable oil and the amount of recoverable gas of rock in the effective thickness interval per unit area on the basis of the amount of recoverable oil and gas per unit mass of rock, logging spacing, rock density and the effective thickness interval.

In one embodiment, the module for establishing a model of an abundance value of a recoverable oil resource and a model of an abundance value of a recoverable gas resource in the effective thickness interval is further used for respectively establishing the model of the abundance value of the recoverable oil resource and the model of the abundance value of the recoverable gas resource in the effective shale interval according to the following formulas:

$$AOR = 10^{13} \times \sum_{i=1}^{n} (Q_{po\_i} \times L_{inter} \times \rho_i);$$

-continued $$AGR = 10^{14} \times \sum_{i=1}^{n}(Q_{pg\_i} \times L_{inter} \times \rho_i);$$

wherein AOR is the abundance of the recoverable oil resource in the effective shale interval of the region to be evaluated, 10,000 tons/km$^2$; AGR is the abundance of the recoverable gas resource in the effective shale interval of the region to be evaluated, 100 million cubic meters/km$^2$; $Q_{po\_i}$ is the amount of recoverable oil per unit mass of rock of an ith logging point in the effective thickness interval of the region to be evaluated, mg/g·rock; $Q_{pg\_i}$ is the amount of recoverable gas per unit mass of rock of the ith logging point in the effective thickness interval of the region to be evaluated, m$^3$/t·rock; $\rho_i$ is the rock density value of the ith logging point in the effective thickness interval of the region to be evaluated, g/cm$^3$; $L_{inter}$ is the logging spacing of the evaluated well, m; n is the total number of logging points in the effective thickness interval, and n is an integer.

In one embodiment, the module for establishing a model of an abundance value of a recoverable oil resource and a model of an abundance value of a recoverable gas resource in the effective thickness interval includes a unit for acquiring the amount of recoverable oil per unit mass of rock and the amount of recoverable gas per unit mass of rock of a logging interpretation point, used for:

acquiring the total organic carbon content, the rock density value and the measured spacing value of the logging interpretation point in the effective shale interval on the basis of the total organic carbon content of the region to be evaluated interpreted by logging, and then, acquiring the amount of recoverable oil per unit mass of rock and the amount of recoverable gas per unit mass of rock of the logging interpretation point by the prediction model of the amount of recoverable oil from in situ conversion of shale and the prediction model of the amount of recoverable gas from in situ conversion of shale on the basis of the total organic carbon content, the rock density value and the measured spacing value of the logging interpretation point in the effective shale interval and the vitrinite reflectance of a well point in a target stratum.

In one embodiment, the module for establishing a prediction model of the amount of a recoverable oil resource and a prediction model of the amount of a recoverable gas resource is specifically used for, on the basis of the abundance of the recoverable oil and gas resources of grid points of the effective shale distribution region and the area of the effective shale distribution region, respectively establishing the prediction model of the amount of the recoverable oil resource and the prediction model of the amount of the recoverable gas resource according to the following formulas:

$$NO = \sum_{j=1}^{m}(AOR_j \times A_j);$$

$$NG = \sum_{j=1}^{m}(AGR_j \times A_j);$$

wherein NO is the amount of the recoverable oil resource in the region to be evaluated, 10,000 tons; NG is the amount of the recoverable gas resource in the region to be evaluated, 100 million cubic meters; $AOR_j$ is the abundance of the recoverable oil resource of a jth grid in the effective shale distribution region, 10,000 tons/ km$^2$; $AGR_j$ is the abundance of the recoverable gas resource of the jth grid in the effective shale distribution region, 100 million cubic meters/km$^2$; $A_j$ is the area of the jth grid in the effective shale distribution region, km$^2$; m is the number of grids in the effective shale distribution region, and m is an integer.

What is described above is only a specific embodiment of the present disclosure and cannot be used to limit the scope of the implementation of the disclosure. Therefore, the replacement of equivalent components or equivalent changes and modifications according to the scope of protection of the patent of the present disclosure shall still fall within the scope of this patent. In addition, in the present disclosure, technical features and technical features, technical features and technical disclosures, and technical disclosures and technical disclosures can be freely combined for use.

What is claimed is:

1. A method for predicting the amount of recoverable oil and gas resources from in-situ conversion of shale, wherein the method for predicting the amount of recoverable oil and gas resources from in-situ conversion of shale comprising:

acquiring a total organic carbon content and vitrinite reflectance of shale to be measured in a region to be evaluated;

establishing a prediction model of the amount of recoverable oil from in-situ conversion of shale, and acquiring the amount of recoverable oil of the shale to be measured on the basis of the total organic carbon content and the vitrinite reflectance of the shale to be measured by using the prediction model of the amount of recoverable oil from in-situ conversion of shale;

wherein establishing a prediction model of the amount of recoverable oil from in-situ conversion of shale comprises: establishing a relationship model between the amount of output oil and the total organic carbon content on the basis of data of the amount of output oil acquired by performing thermal simulation experiments on a plurality of different shale samples, and the total organic carbon content and the vitrinite reflectance of the shale samples, and then extracting empirical parameters in the model to establish a model with the vitrinite reflectance, so as to establish the prediction model of the amount of recoverable oil from in-situ conversion of shale;

establishing a prediction model of the amount of recoverable gas from in-situ conversion of shale, and acquiring the amount of recoverable gas of the shale to be measured on the basis of the total organic carbon content and the vitrinite reflectance of the shale to be measured by using the prediction model of the amount of recoverable gas from in-situ conversion of shale;

wherein establishing a prediction model of the amount of recoverable gas from in-situ conversion of shale comprises:

establishing a relationship model between the amount of output gas and the total organic carbon content on the basis of data of the amount of output gas acquired by performing thermal simulation experiments on a plurality of different shale samples, and the total organic carbon content and the vitrinite reflectance of the shale samples, and then extracting empirical parameters in the model to establish a model with the vitrinite reflectance, so as to establish the prediction model of the amount of recoverable gas from in-situ conversion of shale;

wherein acquiring the data of the amount of output oil and the data of the amount of output gas comprises: loading the shale samples into a reactor separately, and repeatedly compacting the shale samples with 20 MPa pressure, weighing the mass of the shale samples in the reactor before the thermal simulation experiments, and then vacuumizing the reactor and injecting He; performing the thermal simulation experiments on the shale samples at 11 preset temperature points, namely 250° C., 300° C., 320° C., 335° C., 350° C., 360° C., 390° C., 440° C., 500° C., 540° C. and 580° C.; wherein for a first preset temperature point at a temperature of 250° C., a programmed heating rate of 20° C./d is used until the simulation temperature is 200° C.; between 200° C. and 250° C. of a simulation temperature, a programmed heating rate of 5° C./d is used; for the second to eleventh preset temperature points, a programmed heating rate of 20° C./d is used until the simulation temperature reaches the temperature of the previous one preset temperature point of a target preset temperature point; when the simulation temperature is between the temperature of the previous one preset temperature point of the target preset temperature point and the temperature of the target preset temperature point, a programmed heating rate of 5° C./d is used; after the simulation temperature reaches the preset temperature, the preset temperature is maintained and the temperature is constant for 10 hours, and so on, thermal simulation of all preset temperature points is completed; a preset pressure for hydrocarbon discharge is 7 MPa and after completing the thermal simulation experiments, the amount of oil output and the amount of gas output per unit mass of rock at a corresponding preset temperature point were obtained on the basis of the ratio of the amount of output oil and the amount of output gas obtained by collection to the mass of the shale samples before the thermal simulation in a corresponding reactor;

establishing a prediction model of a lower limit value of the total organic carbon content of the effective shale, and acquiring the lower limit value of the total organic carbon content of the effective shale on the basis of a lower limit value of the amount of recoverable oil per unit mass of rock from in-situ conversion of shale and the vitrinite reflectance of the shale to be measured;

determining the effective thickness of shale, an effective thickness interval and an effective shale distribution region from in-situ conversion of shale on the basis of the total organic carbon content of the region to be evaluated interpreted by logging and the lower limit value of the total organic carbon content of the effective shale;

respectively establishing a model of an abundance value of a recoverable oil resource and a model of an abundance value of a recoverable gas resource in the effective thickness interval, and respectively acquiring the abundance value of the recoverable oil resource and the abundance value of the recoverable gas resource in the effective thickness interval of an evaluated well on the basis of the amount of recoverable oil per unit mass of rock and the amount of recoverable gas per unit mass of rock of a logging interpretation point;

respectively establishing a prediction model of the amount of a recoverable oil resource and a prediction model of the amount of a recoverable gas resource, and acquiring the amount of the recoverable oil resource and the amount of the recoverable gas resource on the basis of the prediction model of the amount of a recoverable oil resource and the prediction model of the amount of a recoverable gas resource; and developing in-situ conversion of the shale on the basis of the amount of the recoverable oil resource and the amount of the recoverable gas resource.

2. The method according to claim 1, wherein the prediction model of the amount of recoverable oil from in-situ conversion of shale is established according to the following formula:

$$Q_{po} = a_1 \times \left( \left( e^{a_2 Ro + a_3} \right) TOC - e^{a_4 Ro + a_5} \right) + a_6;$$

wherein, $Q_{po}$ is the amount of recoverable oil of the shale to be measured, mg/g·rock; Ro is the vitrinite reflectance of the shale to be measured, %; TOC is the total organic carbon content of the shale to be measured, wt %; $a_1$, $a_2$, $a_3$, $a_4$, $a_5$ and $a_6$ are the empirical parameters.

3. The method according to claim 1, wherein the prediction model of the amount of recoverable gas from in-situ conversion of shale is established according to the following formula:

$$Q_{pg} = b_1 \times \begin{cases} \left( b_2 e^{b_3 Ro} \right) TOC + b_4 \ln Ro + b_5 & Ro \leq w_1 \\ \left( b_6 \ln Ro + b_7 \right) TOC + b_8 Ro^2 + b_9 Ro + b_{10} & w_1 < Ro \leq w_2 \\ \left( b_{11} Ro^{b_{12}} \right) TOC + b_{13} Ro^2 + b_{14} Ro + b_{15} & Ro \geq w_2 \end{cases};$$

wherein, $Q_{pg}$ is the amount of recoverable gas of the shale to be measured, m³/t·rock; Ro is the vitrinite reflectance of the shale to be measured, %; TOC is the total organic carbon content of the shale to be measured, wt %; $b_1$, $b_2$, $b_3$, $b_4$, $b_5$, $b_6$, $b_7$, $b_8$, $b_9$, $b_{10}$, $b_{11}$, $b_{12}$, $b_{13}$, $b_{14}$ and $b_{15}$ are the empirical parameters; $w_1$ is 0.5%-1.0%, and $w_2$ is 1.0%-1.4%.

4. The method according to claim 1, wherein the lower limit value of the amount of recoverable oil per unit mass of rock from in-situ conversion of shale is acquired on the basis of a lower limit value of the amount of cumulative oil output by any producing well group in the same development region from in-situ conversion of shale and the rock mass of an effective heating region controlled by the producing well group according to the following formula:

$$Q_{po\_limt} = \frac{Q_{oil\_limt}}{Wt_{rock}};$$

wherein, $Q_{po\_limt}$ is the lower limit value of the amount of recoverable oil per unit mass of rock from in-situ conversion of shale, mg/g·rock; $Q_{oil\_limt}$ is the lower limit value of the amount of cumulative oil output by one producing well group from in-situ conversion of shale, mg; $Wt_{rock}$ is the rock mass of the effective heating region controlled by the producing well group from in-situ conversion of shale, g.

5. The method according to claim 4, wherein establishing a prediction model of a lower limit value of the total organic carbon content of the effective shale comprises: on the basis of the prediction model of the amount of recoverable oil from in-situ conversion of shale and the lower limit value of the amount of recoverable oil per unit mass of rock from in-situ conversion of shale, establishing the prediction model of the lower limit value of the total organic carbon content of the effective shale according to the following formula:

$$TOC_{limt} = \frac{c_1 \times Q_{po\_limt} + e^{c_2 Ro + c_3} + c_4}{e^{c_5 Ro + c_6}};$$

wherein, $TOC_{limt}$ is the lower limit value of the total organic carbon content of the effective shale, wt %; $Q_{po\_limt}$ is the lower limit value of the amount of recoverable oil per unit mass of rock from in-situ conversion of shale, mg/g·rock; Ro is the vitrinite reflectance of the shale to be measured, %; $c_1$, $c_2$, $c_3$, $c_4$, $c_5$ and $c_6$ are empirical parameters.

6. The method according to claim 5, wherein the effective thickness of shale, the effective thickness interval and the effective shale distribution region from in-situ conversion of shale are determined on the basis of the total organic carbon content of the region to be evaluated interpreted by logging and the lower limit value of the total organic carbon content of the effective shale according to the following rules:

when the continuous thickness of shale with the total organic carbon content interpreted by logging greater than the lower limit value of the total organic carbon content of the effective shale is greater than a set value of 1-15 m, the set value of 5 m is used as the apparent effective thickness of shale, and a depth interval corresponding to the apparent effective thickness of shale is an apparent effective thickness interval; between two adjacent apparent effective thickness intervals, when the continuous thickness of shale with the total organic carbon content interpreted by logging less than the lower limit value of the total organic carbon content of the effective shale is less than a set value of 0.5-5 m, the set value is determined as 2 m, and this interval is calculated into the apparent effective thickness of shale; when the continuous thickness of shale with the total organic carbon content interpreted by logging less than the lower limit value of the total organic carbon content of the effective shale is greater than a set value of 0.5-5 m, the set value is determined as 2 m, and this interval is not calculated into the apparent effective thickness of shale;

when the apparent effective thickness of shale is greater than a set value of 3-15 m, the set value of 5 m is used as the apparent effective thickness of shale, the apparent effective thickness of shale is the effective thickness of shale, and an interval corresponding to the top and bottom of the effective thickness of shale is the effective thickness interval;

when the apparent effective thickness of shale is less than or equal to a set value of 3-15 m, the set value of 5 m is used as the apparent effective thickness of shale, however, the apparent effective thickness of shale cannot be used as the effective thickness of shale and thus cannot be used as an independently developed interval, and the amount of a recoverable resource is not calculated for this interval; when the longitudinal distance between two or more effective thickness intervals exceeds a preset thickness value of 0.5-5 m, each effective thickness interval will be treated separately as a separate effective thickness interval of shale, i.e., treated as an independent series of development strata;

obtaining the effective thickness distribution of shale in the evaluated region with a non-equidistant interpolation method on the basis of the effective thickness of shale at well points in an evaluated region, wherein the grid spacing of the non-equidistant interpolation method uses a preset value of 0.1-10 km, and when the effective thickness of shale in the evaluated region is greater than a preset value of 3-15 m of the effective thickness, 5 m is used as the boundary of the effective thickness distribution region of shale, and the region where the effective thickness of shale is greater than 5 m is the effective shale distribution region.

7. The method according to claim 1, wherein establishing a prediction model of a lower limit value of the total organic carbon content of the effective shale comprises: on the basis of the prediction model of the amount of recoverable oil from in-situ conversion of shale and the lower limit value of the amount of recoverable oil per unit mass of rock from in-situ conversion of shale, establishing the prediction model of the lower limit value of the total organic carbon content of the effective shale according to the following formula:

$$TOC_{limt} = \frac{c_1 \times Q_{po\_limt} + e^{c_2 Ro + c_3} + c_4}{e^{c_5 Ro + c_6}};$$

wherein, $TOC_{limt}$ is the lower limit value of the total organic carbon content of the effective shale, wt %; $Q_{po\_limt}$ is the lower limit value of the amount of recoverable oil per unit mass of rock from in-situ conversion of shale, mg/g·rock; Ro is the vitrinite reflectance of the shale to be measured, %; $c_1$, $c_2$, $c_3$, $c_4$, $c_5$ and $c_6$ are empirical parameters.

8. The method according to claim 7, wherein the effective thickness of shale, the effective thickness interval and the effective shale distribution region from in-situ conversion of shale are determined on the basis of the total organic carbon content of the region to be evaluated interpreted by logging and the lower limit value of the total organic carbon content of the effective shale according to the following rules:

when the continuous thickness of shale with the total organic carbon content interpreted by logging greater than the lower limit value of the total organic carbon content of the effective shale is greater than a set value of 1-15 m, the set value of 5 m is used as the apparent effective thickness of shale, and a depth interval corresponding to the apparent effective thickness of shale is an apparent effective thickness interval; between two adjacent apparent effective thickness intervals, when the continuous thickness of shale with the total organic carbon content interpreted by logging less than the lower limit value of the total organic carbon content of the effective shale is less than a set value of 0.5-5 m, the set value is determined as 2 m, and this interval is calculated into the apparent effective thickness of shale; when the continuous thickness of shale with the total organic carbon content interpreted by logging less than the lower limit value of the total organic carbon content of the effective shale is greater than a set value of 0.5-5 m, the set value is determined as 2 m, and this interval is not calculated into the apparent effective thickness of shale;

when the apparent effective thickness of shale is greater than a set value of 3-15 m, the set value of 5 m is used as the apparent effective thickness of shale, the apparent effective thickness of shale is the effective thickness of shale, and an interval corresponding to the top and bottom of the effective thickness of shale is the effective thickness interval;

when the apparent effective thickness of shale is less than or equal to a set value of 3-15 m, the set value of 5 m is used as the apparent effective thickness of shale, however, the apparent effective thickness of shale cannot be used as the effective thickness of shale and thus cannot be used as an independently developed interval, and the amount of a recoverable resource is not calculated for this interval; when the longitudinal distance between two or more effective thickness intervals exceeds a preset thickness value of 0.5-5 m, each effective thickness interval will be treated separately as a separate effective thickness interval of shale, i.e., treated as an independent series of development strata;

obtaining the effective thickness distribution of shale in the evaluated region with a non-equidistant interpolation method on the basis of the effective thickness of shale at well points in an evaluated region, wherein the grid spacing of the non-equidistant interpolation method uses a preset value of 0.1-10 km, and when the effective thickness of shale in the evaluated region is greater than a preset value of 3-15 m of the effective thickness, 5 m is used as the boundary of the effective thickness distribution region of shale, and the region where the effective thickness of shale is greater than 5 m is the effective shale distribution region.

9. The method according to claim 1, wherein the effective thickness of shale, the effective thickness interval and the effective shale distribution region from in-situ conversion of shale are determined on the basis of the total organic carbon content of the region to be evaluated interpreted by logging and the lower limit value of the total organic carbon content of the effective shale according to the following rules:

when the continuous thickness of shale with the total organic carbon content interpreted by logging greater than the lower limit value of the total organic carbon content of the effective shale is greater than a set value of 1-15 m, the set value of 5 m is used as the apparent effective thickness of shale, and a depth interval corresponding to the apparent effective thickness of shale is an apparent effective thickness interval; between two adjacent apparent effective thickness intervals, when the continuous thickness of shale with the total organic carbon content interpreted by logging less than the lower limit value of the total organic carbon content of the effective shale is less than a set value of 0.5-5 m, the set value is determined as 2 m, and this interval is calculated into the apparent effective thickness of shale; when the continuous thickness of shale with the total organic carbon content interpreted by logging less than the lower limit value of the total organic carbon content of the effective shale is greater than a set value of 0.5-5 m, the set value is determined as 2 m, and this interval is not calculated into the apparent effective thickness of shale;

when the apparent effective thickness of shale is greater than a set value of 3-15 m, the set value of 5 m is used as the apparent effective thickness of shale, the apparent effective thickness of shale is the effective thickness of shale, and an interval corresponding to the top and bottom of the effective thickness of shale is the effective thickness interval;

when the apparent effective thickness of shale is less than or equal to a set value of 3-15 m, the set value of 5 m is used as the apparent effective thickness of shale, however, the apparent effective thickness of shale cannot be used as the effective thickness of shale and thus cannot be used as an independently developed interval, and the amount of a recoverable resource is not calculated for this interval; when the longitudinal distance between two or more effective thickness intervals exceeds a preset thickness value of 0.5-5 m, each effective thickness interval will be treated separately as a separate effective thickness interval of shale, i.e., treated as an independent series of development strata;

obtaining the effective thickness distribution of shale in the evaluated region with a non-equidistant interpolation method on the basis of the effective thickness of shale at well points in an evaluated region, wherein the grid spacing of the non-equidistant interpolation method uses a preset value of 0.1-10 km, and when the effective thickness of shale in the evaluated region is greater than a preset value of 3-15 m of the effective thickness, 5 m is used as the boundary of the effective thickness distribution region of shale, and the region where the effective thickness of shale is greater than 5 m is the effective shale distribution region.

10. The method according to claim 1, wherein respectively establishing a model of an abundance value of a recoverable oil resource and a model of an abundance value of a recoverable gas resource in an effective shale interval, comprises:

respectively establishing the model of the abundance value of the recoverable oil resource and the model of the abundance value of the recoverable gas resource in the effective shale interval according to the amount of recoverable oil and the amount of recoverable gas of rock in the effective thickness interval per unit area on the basis of the amount of recoverable oil and gas per unit mass of rock, logging spacing, rock density and the effective thickness interval.

11. The method according to claim 10, wherein the model of the abundance value of the recoverable oil resource and the model of the abundance value of the recoverable gas resource in the effective shale interval are respectively established according to the following formulas:

$$AOR = 10^{13} \times \sum_{i=1}^{n}(Q_{po\_i} \times L_{inter} \times \rho_i);$$

$$AGR = 10^{14} \times \sum_{i=1}^{n}(Q_{pg\_i} \times L_{inter} \times \rho_i);$$

wherein AOR is the abundance of the recoverable oil resource in the effective shale interval of the region to be evaluated, 10,000 tons/km²; AGR is the abundance of the recoverable gas resource in the effective shale interval of the region to be evaluated, 100 million cubic meters/km²; $Q_{po\_i}$ is the amount of recoverable oil per unit mass of rock of an ith logging point in the effective thickness interval of the region to be evaluated, mg/g·rock; $Q_{pg\_i}$ is the amount of recoverable gas per unit mass of rock of the ith logging point in the effective thickness interval of the region to be evaluated, m³/t·rock; $\rho_i$ is the rock density value of the ith logging point in the effective thickness interval of the region to be evaluated, g/cm³; $L_{inter}$ is the logging spacing of the evaluated well, m; n is the total number of logging points in the effective thickness interval, and n is an integer.

12. The method according to claim 11, wherein the amount of recoverable oil per unit mass of rock and the amount of recoverable gas per unit mass of rock of the logging interpretation point are acquired according to the following steps:

acquiring the total organic carbon content, the rock density value and the measured spacing value of the logging interpretation point in the effective shale interval on the basis of the total organic carbon content of the region to be evaluated interpreted by logging, and then, acquiring the amount of recoverable oil per unit mass of rock and the amount of recoverable gas per unit mass of rock of the logging interpretation point by using the prediction model of the amount of recoverable oil from in situ conversion of shale and the prediction model of the amount of recoverable gas from in situ conversion of shale on the basis of the total organic carbon content, the rock density value and the measured spacing value of the logging interpretation point in the effective shale interval and the vitrinite reflectance of a well point in a target stratum.

13. The method according to claim 10, wherein the amount of recoverable oil per unit mass of rock and the amount of recoverable gas per unit mass of rock of the logging interpretation point are acquired according to the following steps:

acquiring the total organic carbon content, the rock density value and the measured spacing value of the logging interpretation point in the effective shale interval on the basis of the total organic carbon content of the region to be evaluated interpreted by logging, and then, acquiring the amount of recoverable oil per unit mass of rock and the amount of recoverable gas per unit mass of rock of the logging interpretation point by using the prediction model of the amount of recoverable oil from in situ conversion of shale and the prediction model of the amount of recoverable gas from in situ conversion of shale on the basis of the total organic carbon content, the rock density value and the measured spacing value of the logging interpretation point in the effective shale interval and the vitrinite reflectance of a well point in a target stratum.

14. The method according to claim 1, wherein the amount of recoverable oil per unit mass of rock and the amount of recoverable gas per unit mass of rock of the logging interpretation point are acquired according to the following steps:

acquiring the total organic carbon content, the rock density value and the measured spacing value of the logging interpretation point in the effective shale interval on the basis of the total organic carbon content of the region to be evaluated interpreted by logging, and then, acquiring the amount of recoverable oil per unit mass of rock and the amount of recoverable gas per unit mass of rock of the logging interpretation point by using the prediction model of the amount of recoverable oil from in situ conversion of shale and the prediction model of the amount of recoverable gas from in situ conversion of shale on the basis of the total organic carbon content, the rock density value and the measured spacing value of the logging interpretation point in the effective shale interval and the vitrinite reflectance of a well point in a target stratum.

15. The method according to claim 1, wherein on the basis of the abundance of the recoverable oil and gas resources of grid points of the effective shale distribution region and the area of the effective shale distribution region, the prediction model of the amount of the recoverable oil resource and the prediction model of the amount of the recoverable gas resource are respectively established according to the following formulas:

$$NO = \sum_{j=1}^{m}(AOR_j \times A_j);$$

$$NG = \sum_{j=1}^{m}(AGR_j \times A_j);$$

wherein NO is the amount of the recoverable oil resource in the region to be evaluated, 10,000 tons; NG is the amount of the recoverable gas resource in the region to be evaluated, 100 million cubic meters; $AOR_j$ is the abundance of the recoverable oil resource of a jth grid in the effective shale distribution region, 10,000 tons/km²; $AGR_j$ is the abundance of the recoverable gas resource of the jth grid in the effective shale distribution region, 100 million cubic meters/km²; $A_j$ is the area of the jth grid in the effective shale distribution region, km²; m is the number of grids in the effective shale distribution region, and m is an integer.

* * * * *